(12) United States Patent
Baba-Ahmed et al.

(10) Patent No.: US 10,899,689 B2
(45) Date of Patent: Jan. 26, 2021

(54) METHOD FOR PURIFYING 2-CHLORO-3,3,3-TRIFLUOROPROPENE AND METHOD FOR PREPARING 2,3,3,3-TETRAFLUORO-1-PROPENE

(71) Applicant: Arkema France, Colombes (FR)

(72) Inventors: Abdelatif Baba-Ahmed, Saint-fons (FR); Bertrand Collier, Saint-genis-laval (FR); Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 191 days.

(21) Appl. No.: 16/063,734

(22) PCT Filed: Dec. 14, 2016

(86) PCT No.: PCT/EP2016/080944
§ 371 (c)(1),
(2) Date: Jun. 19, 2018

(87) PCT Pub. No.: WO2017/108518
PCT Pub. Date: Jun. 29, 2017

(65) Prior Publication Data
US 2020/0157029 A1    May 21, 2020

(30) Foreign Application Priority Data

Dec. 23, 2015  (FR) ..................................... 15 63164

(51) Int. Cl.
| C07C 17/386 | (2006.01) |
| C07C 17/383 | (2006.01) |
(Continued)

(52) U.S. Cl.
CPC ............ *C07C 21/18* (2013.01); *C07C 17/383* (2013.01); *C07C 17/386* (2013.01); *C09K 5/045* (2013.01);
(Continued)

(58) Field of Classification Search
None
See application file for complete search history.

(56) References Cited

U.S. PATENT DOCUMENTS

| 4,902,838 A | 2/1990 | Manzer et al. |
| 5,470,422 A | 11/1995 | Mahler et al. |

(Continued)

FOREIGN PATENT DOCUMENTS

| CN | 101528645 A | 9/2009 |
| CN | 102596868 A | 7/2012 |

(Continued)

OTHER PUBLICATIONS

EPO, International Search Report in International Patent Application No. PCT/EP2016/080944 dated Mar. 3, 2017.
(Continued)

*Primary Examiner* — Medhanit W Bahta
(74) *Attorney, Agent, or Firm* — NK Patent Law

(57) ABSTRACT

The invention concerns a method for purifying 2-chloro-3,3,3-trifluoropropene (1233xf) from a first composition comprising 2-chloro-3,3,3-trifluoropropene and at least one of the compounds chosen from the group consisting of E-1-chloro-3,3,3-trifluoro-1-propene (1233zd E), 1,1,1,3,3-pentafluoropropane (245fa) and 1,1,1,3,3,3-hexafluoropropane (236fa), said method comprising the steps of bringing said first composition into contact with at least one organic extractant in order to form a second composition; extractive distillation of said second composition in order to form a third composition comprising at least one of the compounds
(Continued)

chosen from the group consisting of E-1-chloro-3,3,3-trifluoro-1-propene (1233zd E), 1,1,1,3,3-pentafluoropropane (245fa) and 1,1,1,3,3,3-hexafluoropropane (236fa), and said organic extractant; and a stream comprising 2-chloro-3,3,3-trifluoropropene.

15 Claims, 5 Drawing Sheets

(51) Int. Cl.
    *C07C 21/18*      (2006.01)
    *C07C 19/10*      (2006.01)
    *C09K 5/04*      (2006.01)

(52) U.S. Cl.
    CPC .. *C09K 2205/122* (2013.01); *C09K 2205/126* (2013.01)

(56) References Cited

U.S. PATENT DOCUMENTS

| | | | |
|---|---|---|---|
| 6,191,328 B1 | 2/2001 | Kitano et al. | |
| 7,371,309 B2 | 5/2008 | Boehmer et al. | |
| 2003/0116422 A1 | 6/2003 | Boehmer et al. | |
| 2010/0072415 A1* | 3/2010 | Rao | B01J 23/26 252/67 |
| 2012/0123173 A1* | 5/2012 | Hibino | B01J 23/6447 570/176 |
| 2016/0023974 A1 | 1/2016 | Bonnet et al. | |

FOREIGN PATENT DOCUMENTS

| | | |
|---|---|---|
| CN | 105008271 A | 10/2015 |
| EP | 0921109 A1 | 6/1999 |
| EP | 939071 A1 | 9/1999 |
| EP | 0743934 B1 | 11/1999 |
| EP | 0864554 B1 | 9/2002 |
| JP | H10-017501 A | 1/1998 |
| JP | 2012509323 A | 4/2012 |
| JP | 2013521275 A | 6/2013 |
| WO | 1998019982 | 5/1998 |
| WO | 2003068716 A1 | 8/2003 |
| WO | 2007079431 A2 | 7/2007 |
| WO | 2008040969 A2 | 4/2008 |
| WO | 2008054781 A1 | 5/2008 |
| WO | 2009118628 A1 | 10/2009 |
| WO | 2010059493 A1 | 5/2010 |
| WO | 2011059078 A1 | 5/2011 |
| WO | 2012011609 A1 | 1/2012 |
| WO | 2014147311 A1 | 9/2014 |
| WO | 2014147312 A1 | 9/2014 |

OTHER PUBLICATIONS

CNIPA; Office Action for Chinese Patent Application No. 201680073110 dated Aug. 18, 2020, 18 pages.

JPO; Office Action for Japanese Patent Application No. 2018533077 dated Sep. 1, 2020, 4 pages.

* cited by examiner

METHOD FOR PURIFYING 2-CHLORO-3,3,3-TRIFLUOROPROPENE AND METHOD FOR PREPARING 2,3,3,3-TETRAFLUORO-1-PROPENE

CROSS REFERENCE TO RELATED APPLICATIONS

This application is a U.S. National Stage application of International Application No. PCT/EP2016/080944 filed on Dec. 14, 2016, which claims the benefit of French Patent Application No. 1563164 filed on Dec. 23, 2015, the entire content of all of which is incorporated by reference herein.

TECHNICAL FIELD OF THE INVENTION

The invention relates to a process for preparing 2,3,3,3-tetrafluoro-1-propene. More particularly, the invention relates to a process for preparing 2,3,3,3-tetrafluoro-1-propene including the purification and recycling of 2-chloro-3,3,3-tetrafluoropropene also derived from the reaction.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as coolants, heat-transfer fluids, extinguishers, propellants, foaming agents, swelling agents, gaseous dielectrics, polymerization medium or monomer, support fluids, agents for abrasives, drying agents and fluids for power production units. HFOs have been identified as desirable alternatives to HCFC on account of their low ODP (ozone depletion potential) and GWP (global warming potential) values.

Most of the processes for manufacturing hydrofluoroolefins involve a fluorination and/or dehydrohalogenation reaction. This type of reaction is performed in the gas phase and generates impurities which consequently need to be removed in order to obtain the desired compound in a sufficient degree of purity for the targeted applications.

For example, in the context of producing 2,3,3,3-tetrafluoro-1-propene (HFO-1234yf), the presence of impurities such as 1-chloro-3,3,3-trifluoro-1-propene (1233zd), 1,3,3,3-tetrafluoro-1-propene (1234ze) and 1,1,1,3,3-pentafluoropropane (245fa) is observed. These impurities are isomers of the main compounds that are desired to be obtained via the process for producing 2,3,3,3-tetrafluoro-1-propene, besides the latter, i.e. 2-chloro-3,3,3-trifluoro-1-propene (1233xf) and 1,1,1,2,2-pentafluoropropane (245cb). Given the respective boiling points of 1-chloro-3,3,3-trifluoro-1-propene (1233zd), 1,3,3,3-tetrafluoro-1-propene (1234ze) and 1,1,1,3,3-pentafluoropropane (245fa), they accumulate in the loop of the products recycled into the reactor and thus prevent the formation of the products of interest.

Purification of this type of reaction mixture may be performed via various techniques known from the prior art, for instance distillation. However, when the compounds are to be purified have boiling points that are too close or when they form azeotropic or quasi-azeotropic compositions, distillation is not an efficient process. Extractive distillation processes have thus been described.

EP 0 864 554 discloses a process for purifying a mixture comprising 1,1,1,3,3-pentafluoropropane (245fa) and 1-chloro-3,3,3-trifluoro-trans-1-propene (1233zd) by distillation in the presence of a solvent with a boiling point of greater than that of 1-chloro-3,3,3-trifluoro-trans-1-propene.

WO 03/068716 discloses a process for recovering pentafluoroethane from a mixture comprising pentafluoroethane and chloropentafluoroethane by distillation in the presence of hexafluoropropene.

WO 98/19982 also discloses a process for purifying 1,1-difluoroethane by extractive distillation. The process consists in placing an extracting agent in contact with a mixture of 1,1-difluoroethane and vinyl chloride. The extracting agent is chosen from hydrocarbons, alcohols and chlorocarbons with a boiling point of between 10° C. and 120° C.

As mentioned by WO 98/19982, the selection of the extracting agent may prove to be complex depending on the products to be separated. There is thus still a need to develop a particular process for purifying 2-chloro-3,3,3-trifluoropropene.

SUMMARY OF THE INVENTION

In a process for producing 2,3,3,3-tetrafluoro-1-propene, the choice of particular operating conditions makes it possible to promote the presence of certain impurities or of isomers thereof. The presence of impurities such as 1-chloro-3,3,3-trifluoro-1-propene (1233zd) and 1,1,1,3,3-pentafluoropropane (245fa) may be observed. These impurities may derive from side reactions induced by intermediate compounds produced during the production of 2,3,3,3-tetrafluoro-1-propene, and may have physical properties such that the separation thereof with 2-chloro-3,3,3-trifluoropropene (1233xf) may prove to be complex. There is thus a need to treat the reaction loop in order to limit the presence of impurities. In addition, the present invention allows, besides the production of 2,3,3,3-tetrafluoro-1-propene, the recovery and recycling of the 2-chloro-3,3,3-trifluoropropene (1233xf) produced in excellent purity.

According to a first aspect, the present invention provides a process for purifying 2-chloro-3,3,3-trifluoropropene (1233xf) from a first composition comprising 2-chloro-3,3,3-trifluoropropene and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), said process comprising the steps of:

a) placing said first composition in contact with at least one organic extracting agent to form a second composition;

b) extractive distillation of said second composition to form:
   i) a third composition comprising said organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa),
   ii) a stream comprising 2-chloro-3,3,3-trifluoropropene;

c) recovering and separating out said third composition to form a stream comprising said organic extracting agent and a stream comprising said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

Preferably, the stream comprising the organic extracting agent may be recycled into step a). Preferably, the stream comprising said at least one compound chosen from the group consisting of E-1-chloro-3,3,3-trifluoro-1-propene (1233zdE), 1,1,1,3,3-pentafluoropropane (245fa) and 1,1,1, 3,3,3-hexafluoropropane (236fa) may be incinerated or recovered to be able to purify one or more of the products constituting it.

According to a first preferred embodiment, the organic extracting agent separated out in step c) is recycled into step a).

According to a preferred embodiment, said stream comprising 2-chloro-3,3,3-trifluoropropene formed in step b) is recovered at the top of the distillation column and optionally recycled into a process for producing 2,3,3,3-tetrafluoropropene.

According to a preferred embodiment, said organic extracting agent is a solvent chosen from the group consisting of hydrocarbon, halohydrocarbon, alcohol, ketone, amine, ester, ether, aldehyde, nitrile, carbonate, sulfoxide, sulfate, thioalkyl, amide, heterocycle and phosphate or the organic extracting agent is perfluorobutanoic acid.

According to a preferred embodiment, said organic extracting agent has a boiling point of between 50 and 200° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
- $\gamma_{1,S}$ represents the activity coefficient of 2-chloro-3,3,3-trifluoropropene in said organic extracting agent at infinite dilution,
- P1 represents the saturating vapor pressure of 2-chloro-3,3,3-trifluoropropene,
- $\gamma_{2,S}$ represents the activity coefficient of said at least one compound consisting of E-1-chloro-3,3,3-trifluoro-1-propene (1233zdE), 1,1,1,3,3-pentafluoropropane (245fa) and 1,1,1,3,3,3-hexafluoropropane (236fa) in said organic extracting agent at infinite dilution,
- P2 represents the saturating vapor pressure of said at least one compound consisting of E-1-chloro-3,3,3-trifluoro-1-propene (1233zdE), 1,1,1,3,3-pentafluoropropane (245fa) and 1,1,1,3,3,3-hexafluoropropane (236fa), advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0.

In the present patent application, the saturating vapor pressure is considered for a temperature of 25° C.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
- $\gamma_{1,S}$ represents the activity coefficient of 2-chloro-3,3,3-trifluoropropene in said organic extracting agent at infinite dilution,
- P1 represents the saturating vapor pressure of 2-chloro-3,3,3-trifluoropropene,
- $\gamma_{2,S}$ represents the activity coefficient of 1,1,1,3,3-pentafluoropropane (245fa) in said organic extracting agent at infinite dilution,
- P2 represents the saturating vapor pressure of 1,1,1,3,3-pentafluoropropane (245fa); advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0; and
- said organic extracting agent has an absorption capacity $C_{2,S}$ of greater than or equal to 0.20, the absorption capacity being calculated by the formula $C_{2,S}=1/(\gamma_{2,S})$ in which $\gamma_{2,S}$ represents the activity coefficient of 1,1,1,3,3-pentafluoropropane (245fa) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0.

Thus, according to a particular embodiment, said organic extracting agent may be chosen from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, n,n-dimethylpropanamide, dimethyl malonate, diethyl sulfoxide, 2-(2-methoxyethoxy)ethanol, trimethyl phosphate and diethyl malonate; preferably, said organic extracting agent may be chosen from the group consisting of propanone, methyl acetate, ethyl acetate, butanone, dioxane, trimethoxymethane, 1,3-dioxane, 1,3,5-trioxane, 1,2-diaminoethane and 1-methoxy-2-propanol. Preferably, this particular embodiment may allow efficient separation of 2-chloro-3,3,3-trifluoropropene and 1,1,1,3,3-pentafluoropropane (245fa).

According to a particular embodiment, said organic extracting agent may have a separation factor $S_{1,2}$ of greater than or equal to 1.1, said separation factor being calculated by the formula $S_{1,2}=(\gamma_{1,S}*P1)/(\gamma_{2,S}*P2)$ in which
- $\gamma_{1,S}$ represents the activity coefficient of 2-chloro-3,3,3-trifluoropropene in said organic extracting agent at infinite dilution,
- P1 represents the saturating vapor pressure of 2-chloro-3,3,3-trifluoropropene,
- $\gamma_{2,S}$ represents the activity coefficient of E-1-chloro-3,3,3-trifluoro-1-propene (1233zdE) in said organic extracting agent at infinite dilution,
- P2 represents the saturating vapor pressure of E-1-chloro-3,3,3-trifluoro-1-propene (1233zdE);
- advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0; and
- said organic extracting agent may have an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of E-1-chloro-3,3,3-trifluoro-1-propene (1233zdE) in said organic extracting agent at infinite dilution; advantageously, the absorption capacity $C_{2,S}$ is greater than or equal to 0.40, preferably greater than or equal to 0.60, more preferentially greater than or equal to 0.8, in particular greater than or equal to 1.0.

Thus, in a particular embodiment, said organic extracting agent may be chosen from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, -dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-n-(2-methoxyethyl) ethanamine, 2-(ethylamino)ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-propyl-1-methoxypropanoate, 1,5-pentanediamine, cycloheptanone, 3,4-dimethylpyridine, 1-octanamine, benzylmethylamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine; preferably, said organic extracting agent is chosen from the group consisting of diethylamine, propanone, methyl acetate, tetrahydrofuran, ethyl acetate, butanone, diethoxymethane, isopropyl acetate, tert-butyl acetate, dioxane, 3-pentanone, 1,1-diethoxyethane, 2-pentanone, n-pentylamine, 1,3-dioxane, sec-butyl acetate, 1,2-diaminoethane, 1-methoxy-2-propanol, n-butyl acetate and 1-ethoxy-2-propanol. Preferably, this particular embodiment may allow efficient separation of 2-chloro-3,3,3-trifluoropropene and E-1-chloro-3,3,3-trifluoro-1-propene (1233zdE).

According to a particular embodiment, said organic extracting agent may be chosen from the group consisting of propanone, methyl acetate, ethyl acetate, butanone, dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, n,n-dimethylpropanamide, diethyl sulfoxide, 2-(2-methoxyethoxy)ethanol, trimethyl phosphate and diethylmalonate; preferably, said organic extracting agent may be chosen from the group consisting of propanone, methyl acetate, ethyl acetate, butanone, dioxane, trimethoxymethane, 1,3-dioxane, 1,2-diaminoethane, 1-methoxy-2-propanol, 3-methoxy-1-butanol and diacetone alcohol. Preferably, this particular embodiment may allow efficient and simultaneous separation of 2-chloro-3,3,3-trifluoropropene, E-1-chloro-3,3,3-trifluoro-1-propene (1233zdE) and 1,1,1,3,3-pentafluoropropane (245fa).

According to a particular embodiment, the first composition is an azeotropic or quasi-azeotropic composition comprising 2-chloro-3,3,3-trifluoropropene and E-1-chloro-3,3,3-trifluoro-1-propene (1233zdE); or the first composition is an azeotropic or quasi-azeotropic composition comprising 2-chloro-3,3,3-trifluoropropene and 1,1,1,3,3-pentafluoropropane (245fa).

According to a second aspect of the present invention, a process for producing 2,3,3,3-tetrafluoro-1-propene is provided. Said process comprises the steps of:

A) in a reactor, fluorination in the presence of a catalyst for a compound of formula $CX(Y)_2$—$CX(Y)_m$—$CH_mXY$ (I) in which X and Y independently represent H, F or Cl and m=0 or 1; and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream, preferably derived from purging of the recycling reaction loop, comprising 1,1,1,2,2-pentafluoropropane, 2-chloro-3,3,3-trifluoropropene, and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), C) distillation of the stream recovered in step B) and recovery, at the top of the distillation column, of a stream comprising 1,1,1,2,2-pentafluoropropane and, at the bottom of the distillation column, of a stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), D) performing the process for purifying 2-chloro-3,3,3-trifluoropropene according to the present invention using the stream recovered in step C) and comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa); and E) recycling into step A) the stream comprising the 2-chloro-3,3,3-trifluoropropene formed and recovered in step b) of the purification process performed in step D).

According to a preferred embodiment, the stream comprising 1,1,1,2,2-pentafluoropropane recovered in step C) at the top of the distillation column may be recycled, for example in the reaction loop, i.e. in step A).

Preferably, the process for producing 2,3,3,3-tetrafluoro-1-propene is performed in a device comprising a reactor and a recycling reaction loop. Said loop may be purged.

According to a preferred embodiment, the stream recovered in step B) also comprising HF, 1,1,1,2,2-pentafluoropropane and 1,3,3,3-tetrafluoro-1-propene (1234ze), the latter being, prior to performing the distillation of step C), treated according to the following steps:

i) low-temperature separation of said liquid composition to form a first HF-rich phase and a second organic phase containing 1,3,3,3-tetrafluoro-1-propene (1234ze), 1,1,1,2,2-pentafluoropropane and 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);

ii) distillation of said second organic phase to form and recover, advantageously at the top of the distillation column, a first stream comprising 1,1,1,2,2-pentafluoropropane and 1,3,3,3-tetrafluoro-1-propene (1234ze), and to form and recover, advantageously at the bottom of the distillation column, a second stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);

iii) recovery of said second stream and implementation of step D) using same.

According to another aspect, the invention provides a process comprising 2-chloro-3,3,3-trifluoropropene (1233xf), E-1-chloro-3,3,3-trifluoro-1-propene (1233zdE) and an organic extracting agent with a separation factor $S_{1,2}$ of greater than or equal to 1.6, said separation factor being calculated by the formula $S_{1,2}=(\gamma_{1,S}*P1)/(\gamma_{2,S}*P2)$ in which $\gamma_{1,S}$ represents the activity coefficient of 2-chloro-3,3,3-trifluoropropene (1233xf) in said organic extracting agent at infinite dilution, P1 represents the saturating vapor pressure of 2-chloro-3,3,3-trifluoropropene (1233xf), $\gamma_{2,S}$ represents the activity coefficient of E-1-chloro-3,3,3-trifluoro-1-propene (1233zdE) in said organic extracting agent at infinite dilution, P2 represents the saturating vapor pressure of E-1-chloro-3,3,3-trifluoro-1-propene (1233zdE), preferably, said organic extracting agent has an absorption capacity $C_{2,S}$ of greater than or equal to 1.0, said absorption capacity being calculated by the formula $C_{2,S}=1/(\gamma_{2,S})$ in which $\gamma_{2,S}$ represents the activity coefficient of E-1-chloro-3,3,3-trifluoro-1-propene (1233zdE) In said organic extracting agent at infinite dilution; preferably, said organic extracting agent is chosen from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, -dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-n-(2-methoxyethyl)ethanamine, 2-(ethylamino)ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-propyl-1-methoxypropanoate, 1,5-pentanediamine, cycloheptanone, 3,4-dimethylpyridine, 1-octanamine, benzylmethylamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine; in particular, said organic extracting agent is chosen from the group consisting of diethylamine, propanone, methyl acetate, tetrahydrofuran, ethyl acetate, butanone, diethoxymethane, isopropyl acetate, tert-butyl acetate, dioxane, 3-pentanone, 1,1-diethoxyethane, 2-pentanone, n-pentylamine, 1,3-dioxane, sec-butyl acetate, 1,2-diaminoethane, 1-methoxy-2-propanol, n-butyl acetate and 1-ethoxy-2-propanol.

According to another aspect, the invention provides a composition comprising 2-chloro-3,3,3-trifluoropropene (1233xf), 1,1,1,3,3-pentafluoropropane (245fa) and an organic extracting agent with a separation factor $S_{1,2}$ of greater than or equal to 1.6, said separation factor being calculated by the formula $S_{1,2}=(\gamma_{1,S}*P1)/(\gamma_{2,S}*P2)$ in which $\gamma_{1,S}$ represents the activity coefficient of 2-chloro-3,3,3-trifluoropropene (1233xf) in said organic extracting agent at infinite dilution, P1 represents the saturating vapor pressure of 2-chloro-3,3,3-trifluoropropene (1233xf), $\gamma_{2,S}$ represents the activity coefficient of 1,1,1,3,3-pentafluoropropane (245fa) in said organic extracting agent at infinite dilution, P2 represents the saturating vapor pressure of 1,1,1,3,3-pentafluoropropane (245fa), preferably, said organic extracting agent has an absorption capacity $C_{2,S}$ of greater than or equal to 1.0, said absorption capacity being calculated by the formula $C_{2,S}=1/(\gamma_{2,S})$ in which $\gamma_{2,S}$ represents the activity coefficient of 1,1,1,3,3-pentafluoropropane (245fa) in said organic extracting agent at infinite dilution; preferably, said organic extracting agent is chosen from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, n,n-dimethylpropanamide, dimethyl malonate, diethyl sulfoxide, 2-(2-methoxyethoxy)ethanol, trimethyl phosphate and diethyl malonate; in particular, said organic extracting agent is chosen from the group consisting of propanone, methyl acetate, ethyl acetate, butanone, dioxane, trimethoxymethane, 1,3-dioxane, 1,3,5-trioxane, 1,2-diaminoethane and 1-methoxy-2-propanol.

According to another aspect, the invention provides an azeotropic or quasi-azeotropic composition comprising 45 mol % to 65 mol % of 2-chloro-3,3,3-trifluoropropene (1233xf) and from 35 mol % to 55 mol % of 1,1,1,3,3-pentafluoropropane (245fa) relative to the total composition.

According to another aspect, the invention provides a composition comprising 2-chloro-3,3,3-trifluoropropene (1233xf), 1,1,1,3,3-pentafluoropropane (245fa) and E-1-chloro-3,3,3-trifluoro-1-propene (1233zdE) and an organic extracting agent chosen from the group consisting of propanone, methyl acetate, ethyl acetate, butanone, dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, n,n-dimethylpropanamide, diethyl sulfoxide, 2-(2-methoxyethoxy)ethanol, trimethyl phosphate and diethyl malonate; preferably, an organic extracting agent chosen from the group consisting of propanone, methyl acetate, ethyl acetate, butanone, dioxane, trimethoxymethane, 1,3-dioxane, 1,2-diaminoethane, 1-methoxy-2-propanol, 3-methoxy-1-butanol and diacetone alcohol.

DETAILED DESCRIPTION OF THE INVENTION

Figure 1A:
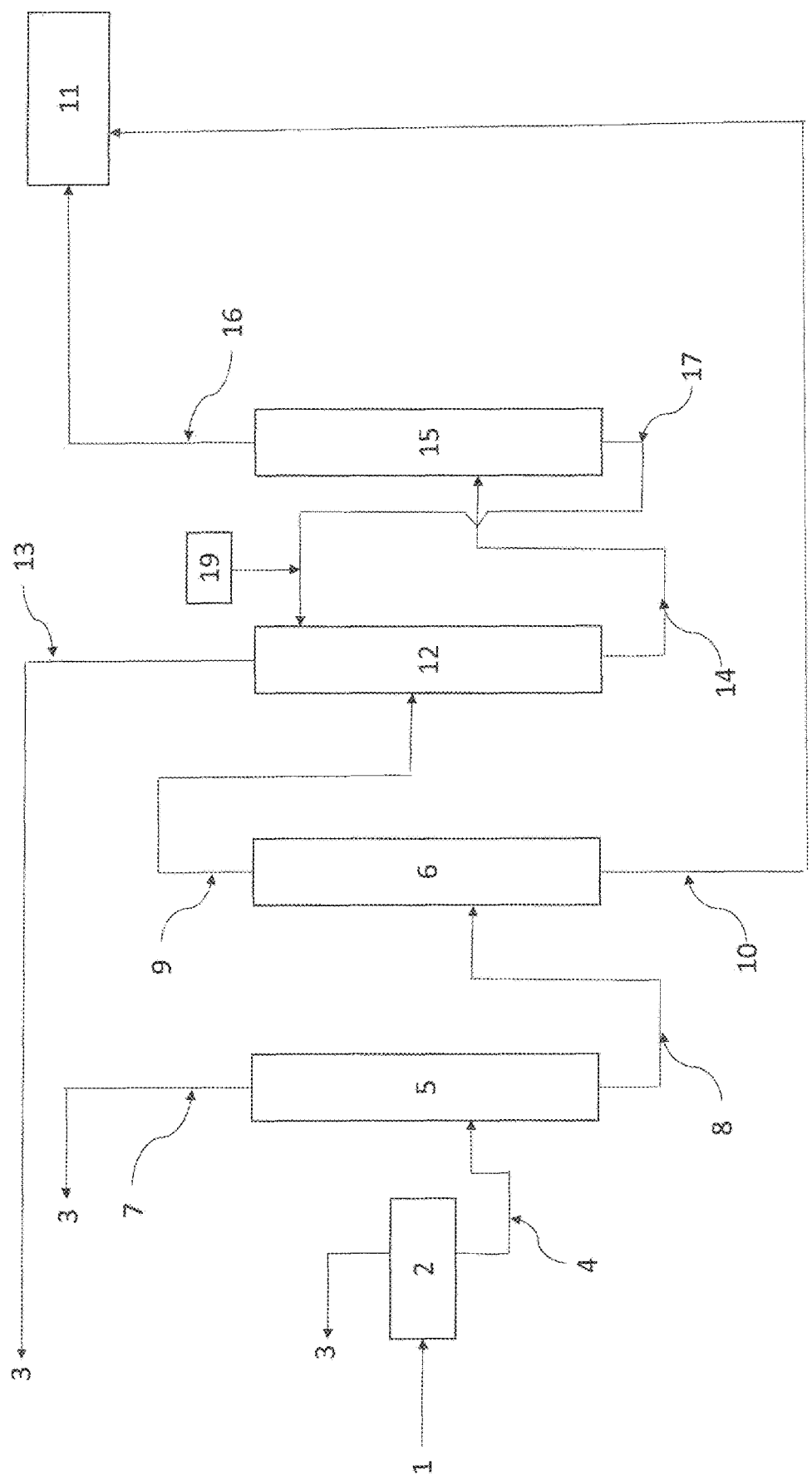
FIGS. 1a-d schematically represent a device for performing a process for purifying 2-chloro-3,3,3-trifluoropropene according to particular embodiments of the present invention.

The term "hydrocarbon" as used herein refers to linear or branched $C_1$-$C_{20}$ alkane, $C_3$-$C_{20}$ cycloalkane, $C_5$-$C_{20}$ alkene, $C_5$-$C_{20}$ cycloalkene or $C_6$-$C_{18}$ arene compounds. For example, the term "alkane" refers to compounds of formula $C_nH_{2n+2}$ in which n is between 1 and 20. The term "$C_1$-$C_{20}$ alkane" includes, for example, pentane, hexane, heptane, octane, nonane and decane, or isomers thereof. The term "$C_5$-$C_{20}$ alkene" refers to hydrocarbon-based compounds comprising one or more carbon-carbon double bonds and comprising from 5 to 20 carbon atoms. The term "$C_3$-$C_{20}$ cycloalkane" refers to a saturated hydrocarbon-based ring comprising from 3 to 20 carbon atoms. The term "$C_6$-$C_{18}$ aryl" refers to cyclic and aromatic hydrocarbon-based compounds comprising from 6 to 18 carbon atoms. The term "$C_5$-$C_{20}$ cycloalkene" refers to cyclic hydrocarbon-based compounds comprising from 5 to 20 carbon atoms and comprising one or more carbon-carbon double bonds.

The term "alkyl" denotes a monovalent radical derived from a linear or branched alkane, comprising from 1 to 20 carbon atoms. The term "cycloalkyl" denotes a monovalent radical derived from a cycloalkane, comprising from 3 to 20 carbon atoms. The term "aryl" denotes a monovalent radical derived from an arene, comprising from 6 to 18 carbon atoms. The term "alkenyl" denotes a monovalent radical of 2 to 20 carbon atoms and at least one carbon-carbon double bond. The term "alkynyl" denotes a monovalent radical of 2 to 20 carbon atoms and at least one carbon-carbon triple bond. The term "halogen" refers to an —F, —Cl, —Br or —I group. The term "cycloalkenyl" refers to a monovalent radical derived from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —P(O)(OR$^a$)$_2$, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ or —S(O)R$^a$ substituents in which R$^a$ and R$^b$ are, independently of each other, hydrogen, unsubstituted $C_1$-$C_{20}$ alkyl, unsubstituted $C_2$-$C_{20}$ alkenyl, unsubstituted $C_2$-$C_{20}$ alkynyl, unsubstituted $C_3$-$C_{20}$ cycloalkyl, unsubstituted $C_3$-$C_{20}$ cycloalkenyl or unsubstituted $C_6$-$C_{18}$ aryl. In the substituents —NR$^a$R$^b$, R$^a$ and R$^b$ may form, with the nitrogen atom to which they are attached, a saturated or unsaturated, aromatic or non-aromatic, 5- to 10-membered heterocycle.

The term "halohydrocarbons" refers to compounds of formula R$^a$X in which R$^a$ is chosen from $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl and X represents a chlorine, fluorine, bromine or iodine atom. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —P(O)(OR$^a$)$_2$, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ or —S(O)R$^a$ substituents in which R$^a$ and R$^b$ are as defined above.

The term "alcohol" refers to hydrocarbons or halohydrocarbons as defined above in which at least one hydrogen atom is replaced with a hydroxyl group —OH.

The term "ketone" refers to hydrocarbons comprising at least one or more carbonyl functional groups R$^c$—C(O)—R$^d$ in which R$^c$ and R$^d$ are, independently of each other, a $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl or $C_6$-$C_{18}$ aryl and may be optionally substituted with one or more —OH, halogen, —P(O)(OR$^a$)$_2$, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ or —S(O)R$^a$ substituents in which R$^a$ and R$^b$ are defined above, R$^c$ and R$^d$ which may be linked together to form, with the carbonyl group to which they are attached, a 4- to 10-membered and preferably 4- to 7-membered cyclic ketone. The cyclic ketone may also comprise one or more carbon-carbon double bonds. The cyclic ketone may also be optionally substituted with one or more substituents as defined above.

The term "amine" refers to hydrocarbons comprising at least one or more amine functional groups —NR$^c$R$^d$ in which R$^c$ and R$^d$ are as defined above, R$^c$ and R$^d$ possibly being linked together to form, with the nitrogen atom to which they are attached, a 4- to 10-membered aromatic or non-aromatic heterocycle.

The term "esters" refers to compounds of formula R$^c$—C(O)—O—R$^d$ in which R$^c$ and R$^d$ are as defined above, R$^c$ and R$^d$ possibly being linked together to form, with the ester group, a ring comprising from 4 to 20 carbon atoms.

The term "ether" refers to compounds of formula R$^c$—O—R$^d$ in which R$^c$ and R$^d$ are as defined above, R$^c$ and R$^d$ possibly being linked together to form, with the oxygen atom to which they are attached, a heterocycle comprising from 4 to 20 carbon atoms.

The term "aldehyde" refers to compounds comprising at least one or more —C(O)—H functional groups.

The term "nitrile" refers to compounds comprising at least one or more —CN functional groups.

The term "carbonate" refers to compounds of formula $R^c$—O—C(O)—O—$R^d$ in which $R^c$ and $R^d$ are as defined above.

The term "sulfoxide" refers to compounds of formula $R^c$S(O)$R^d$ in which $R^c$ and $R^d$ are as defined above.

The term "sulfate" refers to compounds of formula $R^c$S(O)$_2$$R^d$.

The term "thioalkyl" refers to compounds of formula $R^c$SR$^d$ in which $R^c$ and $R^d$ are as defined above.

The term "amide" relates to compounds of formula $R^c$C(O)NR$^e$R$^d$ in which $R^c$ and $R^d$ are as defined above, $R^e$ being defined by the same substituents as $R^c$, $R^c$ and $R^d$ possibly being linked together to form, with the amide group —C(O)N— to which they are attached, a 4- to 10-membered and preferably 4- to 7-membered cyclic amide. The cyclic amide may also comprise one or more carbon-carbon double bonds. The cyclic amide may also be optionally substituted with one or more substituents as defined above.

The term "heterocycle" denotes a 4- to 10-membered carbon-based ring, at least one of the ring members of which is a heteroatom chosen from the group consisting of O, S, P and N. The ring may comprise one or more carbon-carbon double bonds or one or more carbon-heteroatom double bonds or one or more heteroatoms-heteroatom double bonds. Preferably, the heterocycle may comprise 1, 2, 3, 4 or 5 heteroatoms as defined above. In particular, the heterocycle may comprise 1, 2 or 3 heteroatoms chosen from oxygen, nitrogen and sulfur. Preferably, the heterocycle may be a 4- to 6-membered carbon-based ring, 1, 2 or 3 ring members of which are heteroatoms chosen from O and N; preferably O. The heterocycle may be optionally substituted with one or more substituents chosen from —OH, halogen, —P(O)(OR$^a$)$_2$, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ and —S(O)R$^a$ in which R$^a$ and R$^b$ are as defined above.

The term "phosphate" refers to compounds of formula (R$^c$O)$_3$P(O) in which R$^c$ is as defined above.

The term "azeotropic composition" denotes a liquid mixture of two or more compounds which behave like a single substance, and which boils at a fixed temperature maintaining a composition in the liquid phase identical to that in the gas phase. The term "quasi-azeotropic composition" denotes a liquid mixture of two or more compounds having a constant boiling point or which has a tendency not to fractionate when it is subjected to boiling or to evaporation.

According to a first aspect, the invention relates to a process for purifying 2-chloro-3,3,3-trifluoropropene (1233xf). The purification process is performed starting with a first composition comprising 2-chloro-3,3,3-trifluoropropene and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

Preferably, said process comprises the steps of:
a) placing said first composition in contact with at least one organic extracting agent to form a second composition;
b) extractive distillation of said second composition to form:
i) a third composition comprising said organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa),
ii) a stream comprising 2-chloro-3,3,3-trifluoropropene;
c) recovering and separating out said third composition to form a stream comprising said organic extracting agent and and a stream comprising said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

Alternatively, step c) may be optional.

Preferably, the stream comprising said organic agent is recycled into step a).

Preferably, the stream comprising said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) is incinerated or recovered to extract and purify one of the constituents thereof.

Said first composition may comprise 2-chloro-3,3,3-trifluoropropene and at least one, at least two or all of the compounds chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

Said first composition may comprise between 50% and 99.99% by weight of 2-chloro-3,3,3-trifluoropropene relative to the total weight of the first composition, advantageously between 55% and 99.9% by weight, preferably between 55% and 95% and in particular between 60% and 90% by weight of 2-chloro-3,3,3-trifluoropropene relative to the total weight of the first composition.

When it contains same, said first composition may comprise between 0.01% and 50% by weight of E-1-chloro-3,3,3-trifluoro-1-propene (1233zdE) relative to the total weight of the first composition, advantageously between 0.01% and 40% by weight, preferably between 0.01% and 30% and in particular between 0.01% and 20% by weight of E-1-chloro-3,3,3-trifluoro-1-propene (1233zdE) relative to the total weight of the first composition.

When it contains same, said first composition may comprise between 0.01% and 50% by weight of 1,1,1,3,3-pentafluoropropane (245fa) relative to the total weight of the first composition, advantageously between 0.01% and 40% by weight, preferably between 0.01% and 30% and in particular between 0.01% and 20% by weight of 1,1,1,3,3-pentafluoropropane (245fa) relative to the total weight of the first composition.

When it contains same, said first composition may comprise between 0.01% and 15% by weight of 1,1,1,3,3,3-hexafluoropropane (236fa) relative to the total weight of the first composition, advantageously between 0.01% and 10% by weight, preferably between 0.01% and 7% and in particular between 0.01% and 5% by weight of 1,1,1,3,3,3-hexafluoropropane (236fa) relative to the total weight of the first composition.

According to a particular embodiment, said organic extracting agent is a solvent chosen from the group consisting of hydrocarbon, halohydrocarbon, alcohol, ketone, amine, ester, ether, aldehyde, nitrile, carbonate, sulfoxide, sulfate, thioalkyl, amide, heterocycle and phosphate. Said organic extracting agent may also be perfluorobutanoic acid. Preferably, said organic extracting agent is a solvent chosen from the group consisting of alcohol, ketone, amine, ester, ether, aldehyde, carbonate, sulfoxide, amide, heterocycle and phosphate.

Said organic extracting agent refers to a compound comprising at least one carbon atom.

Preferably, the hydrocarbons are chosen from the group consisting of cyclohexene, 1,3,5-triethylbenzene, 2,4,4-trimethyl-1-pentene, 1-methylcyclohexene, 1,4-dimethylbenzene, styrene, 1,3,5-trimethylbenzene, 1,2,4,5-tetramethylbenzene and 1,3-diethenylbenzene.

Preferably, the halohydrocarbons are chosen from the group consisting of 2-chloro-2-methylpropane, 1-chloro-2,2-difluoropropane, 1,1-dichloroethane, 2-bromopropane, 2-chlorobutane, 1-bromopropane, 2-bromo-2-methylpropane, 1-chloro-3-fluoropropane, 1-chlorobutane, 2-chloro-2-methylbutane, 1,2-dichloroethane, 1,1-dichloropropane, 1,2-dichloro-2-fluoropropane, 2-bromobutane, 1-fluorohexane, 2,3-dichloro-1-propene, 1,2-dichloropropane, 3-chloropentane, trichloroacetaldehyde, isoamyl chloride, 1-chloro-4-fluorobutane, 1-bromo-3-fluoropropane, 1-bromobutane, 2,2-dichlorobutane, cis-1,3-dichloropropene, 2-bromo-2-methylbutane, trans-1,3-dichloropropene, 1,1,1-trichloro-3-fluoropropane, 1-chloro-3,3-dimethylbutane, 2-bromopentane, 2,3-dichlorobutane, 1-bromo-3-methylbutane, 1,3-dichloro-trans-2-butene, 1,3-dichloropropane, 1,2,2-trichloropropane, 1,2-dichlorobutane, 2,3-dichloro-2-methylbutane, 1-bromopentane, 1,2-dichloro-2-butene, 1,3-dichlorobutane, 1-chloro-3-bromopropane, 1,2-dichloropentane, 1-bromohexane, 1,2,3-trichloropropane, 1,4-dichloro-trans-2-butene, 1,4-dichlorobutane, 2-chloropyridine, bromocyclohexane, 1,3-dibromopropane, 1,4-dichlorobenzene, 1-chlorooctane, 1-fluorodecane, 2-chloro-1,4-dimethylbenzene and 1,4-dibromobutane.

Preferably, the alcohols are chosen from the group consisting of methanol, 1,1,1-trifluoro-2-propanol, ethanol, 2-propanol, tert-butanol, 2,2-difluoroethanol, propanol, 2-allyloxyethanol, 2-butanol, 2,2,3,3-tetrafluoro-1-propanol, 1-methoxy-2-propanol, 1-(dimethylamino)-2-propanol, 4,4,4-trifluorobutanol, 3-fluoropropanol, 2-chloroethanol, 2-methoxy-1-propanol, 1-ethoxy-2-propanol, 2-chloro-1-propanol, 2-(dimethylamino)ethanol, 2-ethoxy-1-propanol, 2-propoxyethanol, 1-propoxy-2-propanol, 2-isopropoxyethanol, 2-(methylamino)ethanol, 3-ethoxy-1-propanol, 3-methoxy-1-butanol, 2-(diethylamino)ethanol, 2-(ethylamino)ethanol, 1-butoxy-2-propanol, 2-furanmethanol, 2-butoxyethanol, 2-aminopropanol, 2-amino-1-butanol, 2-methyl-2-nitro-1-propanol, 2-(ethylthio)ethanol, propylene glycol, 2-(2-methoxyethoxy)ethanol, 1,2-butanediol, glycol and 2-methyl-2,4-pentanediol.

Preferably, the ketones are chosen from the group consisting of propanone, butanone, 3-pentanone, 2-pentanone, 3,3-dimethyl-2-butanone, 4-methyl-2-pentanone, 2-hexanone, 5-hexen-2-one, 4-methyl-2-hexanone, 2-heptanone, cyclohexanone, 4-methoxy-4-methylpentan-2-one, 2,3-heptanedione, 3-octanone, diacetone alcohol, 2-octanone, cycloheptanone, dihydroxyacetone and 2-propylcyclohexanone.

Preferably, the amines are chosen from the group consisting of 2-methoxyethanamine, n-methylhydroxylamine, 2-ethoxyethanamine, n-methyl-1,2-ethanediamine, 1,2-diaminoethane, 1,2-propanediamine, 1,3-propanediamine, dimethylethanolamine, 1,4-butanediamine, ethanolamine and diethylpropanolamine.

Preferably, the esters are chosen from the group consisting of methyl acetate, isopropyl formate, ethyl acetate, n-propyl formate, isopropyl acetate, tert-butyl acetate, ethyl propionate, sec-butyl acetate, diethyl carbonate, n-butyl acetate, methyl hexanoate, isopropyl chloroacetate, 2-ethoxyethyl acetate, methyl acetoacetate, methyl heptanoate, 2-propyl-1-methoxypropanoate, dimethyl malonate, dihexyl phthalate, dimethyl sulfate, 2-butoxyethyl acetate, trimethyl phosphate, methyl benzoate and diethyl malonate.

Preferably, the ethers are chosen from the group consisting of chloromethoxymethane, 1,2-dimethoxyethane, trimethoxymethane, 2-methoxyethanol, 2-chloro-1,1-dimethoxyethane, ethoxyethanol, 1-methoxy-2-acetoxypropane, 1,1,3,3-tetramethoxypropane and diethylene glycol monoethyl ether.

Preferably, the aldehydes are chosen from the group consisting of ethanedial, isobutanal, methylglyoxal, 2-methylbutanal, hexanal, heptanal, 3-hydroxybutanal and furfural.

Preferably, the nitriles are chosen from the group consisting of acetonitrile, propionitrile, butyronitrile, valeronitrile, (methyleneamino)acetonitrile and 3-methoxypropanenitrile.

Preferably, the carbonate may be diethyl carbonate.

Preferably, the sulfoxides are chosen from the group consisting of dimethyl sulfoxide and diethyl sulfoxide.

Preferably, the sulfate may be dimethyl sulfate.

Preferably, the amides include dimethylformamide, 2,2,2-trifluoroacetamide and n,n-dimethylpropanamide.

Preferably, the thioalkyl may be 3-mercapto-1,2-propanediol.

Preferably, the heterocycles are chosen from the group consisting of tetrahydrofuran, dioxane, 1,3-dioxane, 1,3,5-trioxane and 3-furfural.

Preferably, the phosphate may be, for example, trimethyl phosphate.

The organic extracting agent to be used may be chosen as a function of the compounds present in said first composition. Thus, the organic extracting agent may be chosen as a function of the separation factor and of the absorption capacity established for a particular composition. Besides these two criteria, the choice of the organic extracting agent may be optionally based on other commercial or environmental criteria, for instance the cost of the organic extracting agent, its availability on the market, and its toxicity or flammability properties. Furthermore, according to a particular embodiment, in order to optimize the functioning of the distillation columns used in the steps b) and c) of the present process for purifying 2-chloro-3,3,3-trifluoropropene, the boiling point of the organic extracting agent may be from 50° C. to 200° C., advantageously from 50° C. to 190° C., preferably from 50° C. to 180° C., in particular from 50° C. to 160° C., preferentially from 50° C. to 150° C. and more preferentially from 75° C. to 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 2-chloro-3,3,3-trifluoropropene in said organic extracting agent at infinite dilution, P1 represents the saturating vapor pressure of 2-chloro-3,3,3-trifluoropropene, $\gamma_{2,S}$ represents the activity coefficient of said at least one compound chosen from the group consisting of E-1-chloro-3,3,3-trifluoro-1-propene (1233zdE) and 1,1,1,3,3-pentafluoropropane (245fa) in said organic extracting agent at infinite dilution, P2 represents the saturating vapor pressure of said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

In the present patent application, the saturating vapor pressure is considered for a temperature of 25° C. Advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0.

Said organic extracting agent may have an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said at least one compound chosen from the group consisting of 1-chloro-3,3,3-trifluoro-1-propene (1233zd), 1,1,1,3,3-pentafluoropropane (245fa) and 1,1,1,3,3,3-hexafluoropropane (236fa) in said organic extracting agent at infinite dilution. Advantageously, the absorption capacity $C_{2,S}$ is greater than or equal to 0.40, preferably greater than or equal to 0.60, more preferentially greater than or equal to 0.80, in particular greater than or equal to 1.0, more particularly greater than or equal to 1.4 and preferentially greater than or equal to 1.6. Thus, said organic extracting agent may have a separation factor $S_{1,2}$ of greater than or equal to 1.1, advantageously greater than or equal to 1.2, preferably greater than or equal to 1.4, more preferentially greater than or equal to 1.6, in particular greater than or equal to 1.8 and more particularly greater than or equal to 2.0; and an absorption capacity $C_{2,S}$ of greater than or equal to 0.20, advantageously greater than or equal to 0.40, preferably greater than or equal to 0.60, more preferentially greater than or equal to 0.8, in particular greater than or equal to 1.0, more particularly greater than or equal to 1.4 and preferentially greater than or equal to 1.6.

Preferably, said organic extracting agent may be chosen from the group consisting of propanone, methyl acetate, ethyl acetate, butanone, dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, n,n-dimethylpropanamide, diethyl sulfoxide, 2-(2-methoxyethoxy)ethanol, trimethyl phosphate and diethyl malonate. In particular, said organic extracting agent may be chosen from the group consisting of propanone, methyl acetate, ethyl acetate, butanone, dioxane, trimethoxymethane, 1,3-dioxane, 1,2-diaminoethane, 1-methoxy-2-propanol, 3-methoxy-1-butanol and diacetone alcohol.

Said first composition may be a composition comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). Said first composition may be a composition comprising 2-chloro-3,3,3-trifluoropropene (1233xf) and at least two or all of the compounds chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). The content of each of the compounds in the first azeotropic or quasi-azeotropic composition is as expressed above.

Depending on the compound(s) to be removed in said first composition, said separation factor and said absorption capacity may be calculated for a particular binary couple consisting of 2-chloro-3,3,3-trifluoropropene (1233xf) and one of the compounds chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). Thus, to select said organic extracting agent that is suitable for use in the extractive distillation step b), the separation factor and the absorption capacity may be calculated, for example, for a 2-chloro-3,3,3-trifluoropropene (1233xf) and 1,1,1,3,3-pentafluoropropane (245fa) binary couple if said first composition comprises these two compounds or for a 2-chloro-3,3,3-trifluoropropene (1233xf) and E-1-chloro-3,3,3-trifluoro-1-propene (1233zdE) binary couple if said first composition comprises these two compounds. The separation factor $S_{1,2}$ makes it possible to determine the capacity of an organic extracting agent to separate two or more compounds. The absorption capacity $C_{2,S}$ makes it possible to determine the amount of solvent to be used to obtain separation between the compounds under consideration. For all of the first compositions detailed below, said organic extracting agent may have a separation factor $S_{1,2}$ of greater than or equal to 1.1, advantageously greater than or equal to 1.2, preferably greater than or equal to 1.4, more preferentially greater than or equal to 1.6, in particular greater than or equal to 1.8 and more particularly greater than or equal to 2.0; and/or said organic extracting agent may have an absorption capacity $C_{2,S}$ of greater than or equal to 0.25, advantageously greater than or equal to 0.5, preferably greater than or equal to 0.75, more preferentially greater than or equal to 1.0, more particularly greater than or equal to 1.4 and preferentially greater than or equal to 1.6.

According to a preferred embodiment, said first composition may be a composition comprising 2-chloro-3,3,3-trifluoropropene (1233xf) and 1,1,1,3,3-pentafluoropropane (245fa). The content of each of the compounds in this particular composition is as expressed above with reference to the individual contents of each of the compounds. Thus, the second composition may comprise 2-chloro-3,3,3-trifluoropropene (1233xf) and 1,1,1,3,3-pentafluoropropane (245fa) and said organic extracting agent. To separate the first composition comprising 2-chloro-3,3,3-trifluoropropene (1233xf) and 1,1,1,3,3-pentafluoropropane (245fa), an organic extracting agent with a separation factor $S_{1,2}$ of greater than or equal to 1.1 and an absorption capacity $C_{2,S}$ of greater than or equal to 0.2 may be used; said organic extracting agent may be chosen from the group consisting of ethanedial, 2-chloro-1,1,1,3-tetrafluoropropane, 1,1,1,2,2,3,4,5,5,5-decafluoropentane, 1-chloro-2,2-difluoropropane, propanone, methyl acetate, ethyl 1,1,2,2-tetrafluoroethyl ether, chloromethoxymethane, isobutanal, methanol, tetrahydrofuran, isopropyl formate, methylglyoxal, 2,2,2-trifluoroethanol, 1,1,1-trifluoro-2-propanol, ethyl acetate, ethanol, butanone, n-propyl formate, 2-propanol, acetonitrile, pentafluoro-1-propanol, tert-butanol, 1,2-dimethoxyethane, isopropyl acetate, 2-methylbutanal, 2-methoxyethanamine, 2,2-difluoroethanol, propanol, tert-butyl acetate, propionitrile, 2-allyloxyethanol, ethyl propionate, 2-butanol, dioxane, 3-pentanone, 2-pentanone, trimethoxymethane, n-methylhydroxylamine, 3,3-dimethyl-2-butanone, 1,3-dioxane, 2,2,3,3-tetraflouro-1-propanol, 2-ethoxyethanamine, sec-butyl acetate, n-methyl-1,2-ethanediamine, 1,3,5-trioxane, 4-methyl-2-pentanone, 1,2-diaminoethane, butyronitrile, 1-methoxy-2-propanol, 1,2-propanediamine, perfluorobutanoic acid, 1-(dimethylamino)-2-propanol, 2-methoxyethanol, 4,4,4-trifluorobutanol, diethyl carbonate, n-butyl acetate, 2-chloro-1,1-dimethoxyethane, 2-hexanone, 3-fluoropropanol, 5-hexen-2-one, 2-methoxy-1-propanol, hexanal, 1-ethoxy-2-propanol, 2-chloro-1-propanol, 2-(dimethylamino)ethanol, ethoxyethanol, 2-ethoxy-1-propanol, 1,3-propanediamine, 3,3,4,4,5,5,6,6-octafluoro-1-pentanol, valeronitrile, (methyleneamino)acetonitrile, 3-furfural, 4-methyl-2-hexanone, 1-methoxy-2-acetoxypropane, methyl hexanoate, 2-propoxyethanol, 1-propoxy-2-propanol, dimethylethanolamine, isopropyl chloroacetate, 2-heptanone, heptanal, dimethylformamide, 2-isopropoxyethanol, cyclohexanone, 2-ethoxyethyl acetate, 3-hydroxybutanal, 2-(methylamino)ethanol, 1,4-butanediamine, 4-methoxy-4-methylpentan-2-one, 3-ethoxy-1-propanol, 3-methoxy-1- butanol, furfural, diglyme, 2,2,2-trifluoroacetamide, 2-(diethylamino)ethanol, 3-methoxypropanenitrile, 2,3-heptanedione, 2-(ethylamino)ethanol, 3-octanone, diacetone alcohol, 1-butoxy-2-propanol, 2-furanmethanol, 2-butoxyethanol, ethanolamine, methyl acetoacetate, 2-octanone, 2-aminopropanol, methyl heptanoate, n,n-dimethylpropanamide, 2-amino-1-butanol, 2-methyl-2-nitro-1-propanol, 2-propyl-1-methoxypropanoate, cycloheptanone, dihydroxyacetone, dimethyl malonate, 1,1,3,3-tetramethoxypropane, 2-(ethylthio)ethanol, dihexyl phthalate, propylene glycol, dimethyl sulfate, dimethyl sulfoxide, diethylpropanolamine, 2-butoxyethyl acetate, diethyl sulfoxide, 2-(2-methoxyethoxy)ethanol, 1,2-butanediol, diethylene glycol monoethyl ether, trimethyl phosphate, 2-methyl-2,4-pentanediol, methyl benzoate and diethyl malonate.

Advantageously, said organic extracting agent may have a separation factor $S_{1,2}$ of greater than or equal to 1.2 and an adsorption capacity $C_{2,S}$ of greater than or equal to 0.4; and may be chosen from the group consisting of ethanedial, propanone, methyl acetate, chloromethoxymethane, isobutanal, methanol, isopropyl formate, methylglyoxal, 2,2,2-trifluoroethanol, 1,1,1-trifluoro-2-propanol, ethyl acetate, ethanol, butanone, n-propyl formate, 2-propanol, acetonitrile, pentafluoro-1-propanol, tert-butanol, 1,2-dimethoxyethane, isopropyl acetate, 2-methylbutanal, 2-methoxyethanamine, tert-butyl acetate, propionitrile, 2-allyloxyethanol, ethyl propionate, dioxane, 3-pentanone, 2-pentanone, trimethoxymethane, 3,3-dimethyl-2-butanone, 1,3-dioxane, 2,2,3,3-tetrafluoro-1-propanol, sec-butyl acetate, n-methyl-1,2-ethanediamine, 1,3,5-trioxane, 4-methyl-2-pentanone, 1,2-diaminoethane, butyronitrile, 1-methoxy-2-propanol, 1,2-propanediamine, perfluorobutanoic acid, 1-(dimethylamino)-2-propanol, 2-methoxyethanol, 4,4,4-trifluorobutanol, diethyl carbonate, n-butyl acetate, 2-hexanone, 3-fluoropropanol, 5-hexen-2-one, 2-methoxy-1-propanol, 1-ethoxy-2-propanol, 2-(dimethylamino)ethanol, ethoxyethanol, 2-ethoxy-1-propanol, 1,3-propanediamine, 3,3,4,4,5,5,6,6-octafluoro-1-pentanol, valeronitrile, (methyleneamino)acetonitrile, 3-furfural, 4-methyl-2-hexanone, 1-methoxy-2-acetoxypropane, methyl hexanoate, 2-propoxyethanol, 1-propoxy-2-propanol, dimethylethanolamine, 2-heptanone, dimethylformamide, 2-isopropoxyethanol, cyclohexanone, 2-ethoxyethyl acetate, 3-hydroxybutanal, 2-(methylamino)ethanol, 4-methoxy-4-methylpentan-2-one, 3-ethoxy-1-propanol, 3-methoxy-1-butanol, furfural, diglyme, 3-methoxypropanenitrile, 2-(ethylamino)ethanol, diacetone alcohol, 1-butoxy-2-propanol, 2-furanmethanol, methyl acetoacetate, 2-aminopropanol, n,n-dimethylpropanamide, 2-amino-1-butanol, 2-methyl-2-nitro-1-propanol, 2-propyl-1-methoxypropanoate, cycloheptanone, dimethyl malonate, 1,1,3,3-tetramethoxypropane, dimethyl sulfate, dimethyl sulfoxide, 2-butoxyethyl acetate, diethyl sulfoxide, 2-(2-methoxyethoxy)ethanol, 1,2-butanediol, diethylene glycol monoethyl ether, trimethyl phosphate, 2-methyl-2,4-pentanediol, methyl benzoate and diethyl malonate.

Preferably, said organic extracting agent may have a separation factor $S_{1,2}$ of greater than or equal to 1.4 and an adsorption capacity $C_{2,S}$ of greater than or equal to 0.6; and may be chosen from the group consisting of ethanedial, propanone, methyl acetate, isobutanal, isopropyl formate, methylglyoxal, ethyl acetate, butanone, n-propyl formate, acetonitrile, 1,2-dimethoxyethane, isopropyl acetate, 2-methoxyethanamine, propionitrile, 2-allyloxyethanol, ethyl propionate, dioxane, 3-pentanone, 2-pentanone, trimethoxymethane, 3,3-dimethyl-2-butanone, 1,3-dioxane, sec-butyl acetate, 1,3,5-trioxane, 1,2-diaminoethane, butyronitrile, 1-methoxy-2-propanol, 1,2-propanediamine, 1-(dimethylamino)-2-propanol, 2-methoxyethanol, diethyl carbonate, 5-hexen-2-one, 2-methoxy-1-propanol, 1-ethoxy-2-propanol, 2-(dimethylamino)ethanol, ethoxyethanol, 2-ethoxy-1-propanol, 1,3-propanediamine, 3,3,4,4,5,5,6,6-octafluoro-1-pentanol, (methyleneamino)acetonitrile, 3-furfural, 1-methoxy-2-acetoxypropane, dimethylethanolamine, dimethylformamide, 2-isopropoxyethanol, cyclohexanone, 2-ethoxyethyl acetate, 3-hydroxybutanal, 2-(methylamino)ethanol, 3-ethoxy-1-propanol, 3-methoxy-1-butanol, furfural, 3-methoxypropanenitrile, diacetone alcohol, methyl acetoacetate, 2-aminopropanol, n,n-dimethylpropanamide, 2-propyl-1-methoxypropanoate, dimethyl malonate, dimethyl sulfoxide, diethyl sulfoxide, 2-(2-methoxyethoxy)ethanol, diethylene glycol monoethyl ether, trimethyl phosphate, 2-methyl-2,4-pentanediol and diethyl malonate.

In particular, said organic extracting agent may have a separation factor $S_{1,2}$ of greater than or equal to 1.6 and an absorption capacity $C_{2,S}$ of greater than or equal to 0.8; and may be chosen from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, 2-methoxyethanol, diethyl carbonate, 2-methoxy-1-propanol, 3-furfural, 1-methoxy-2-acetoxypropane, dimethylformamide, 3-methoxy-1-butanol, furfural, 3-methoxypropanenitrile, diacetone alcohol, methyl acetoacetate, n,n-dimethylpropanamide, dimethyl malonate, dimethyl sulfoxide, diethyl sulfoxide, 2-(2-methoxyethoxy)ethanol, trimethyl phosphate and diethyl malonate.

More particularly, said organic extracting agent may have a separation factor $S_{1,2}$ of greater than or equal to 1.6 and an absorption capacity $C_{2,S}$ of greater than or equal to 1.0; and may be chosen from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, n,n-dimethylpropanamide, dimethyl malonate, diethyl sulfoxide, 2-(2-methoxyethoxy)ethanol, trimethyl phosphate and diethyl malonate.

Advantageously, said organic extracting agent is chosen from the group consisting of propanone, methyl acetate, ethyl acetate, butanone, dioxane, trimethoxymethane, 1,3-dioxane, 1,3,5-trioxane, 1,2-diaminoethane and 1-methoxy-2-propanol.

According to a preferred embodiment, said first composition may be a composition comprising 2-chloro-3,3,3-trifluoropropene (1233xf) and E-1-chloro-3,3,3-trifluoro-1-propene (1233zdE). The content of each of the compounds in this particular composition is as expressed above with reference to the individual contents of each of the compounds. Thus, the second composition may comprise 2-chloro-3,3,3-trifluoropropene (1233xf) and E-1-chloro-3,3-trifluoro-1-propene (1233zdE) and said organic extracting agent. To separate the first composition comprising 2-chloro-3,3,3-trifluoropropene (1233xf) and E-1-chloro-3,3-trifluoro-1-propene (1233zdE), an organic extracting agent with a separation factor $S_{1,2}$ of greater than or equal to 1.1 and an absorption capacity $C_{2,S}$ of greater than or equal to 0.2 may be used; said organic extracting agent may be chosen from the group consisting of isopropylmethylamine, ethanedial, 1,2-dichloro-1,1,3,3,3-pentafluoropropane, 1-chloro-1,2,2,3-tetrafluoropropane, perfluorocyclohexane, 1,1-dichloro-1,2,2,3,3-pentafluoropropane, 2-chloro-2-methylpropane, 3-chloro-1,1,1,3-tetrafluoropropane, 1,1-dichloro-2,2,3,3,3-pentafluoropropane, 2-chloro-1,1,1,3-tetrafluoropropane, 2-propanethiol, 1,3-dichloro-1,1,2,3,3-pentafluoropropane, 1,2-dichloro-3,3,3-trifluoropropene, 1,3-dichloro-1,1,2,2,3-pentafluoropropane, 2-ethoxypropane, 2,2-dichloro-1,1,1,3-tetrafluoropropane, 1-chloro-2,2-difluoropropane, methyl t-butyl ether, diethylamine, propanone, perfluoro-n-hexane, methyl acetate, 1,1-dichloroethane, ethyl 1,1,2,2-tetrafluoroethyl ether, 4-methoxy-2-methyl-2-butanethiol, 2-bromopropane, chloromethoxymethane, 1,2-dichloro-1,2,3,3,4,4-hexafluorocyclobutane, 1,1-dichloro-2,2-difluoroethane, 2,2-dichloro-1,1,3,3-tetrafluoropropane, trichloromethane, difluorodiethylsilane, 2-butanamine, 2,3-dichloro-1,1,1,2-tetrafluoropropane, n-methylpropylamine, 3-methylpentane, 1,1-dichloro-1,2,2,3-tetrafluoropropane, tert-butylthiol, isobutanal, methanol, tetrahydrofuran, 1,3-dichloro-1,1,2,2-tetrafluoropropane, 1,1,1-trichloro-2,2-difluoroethane, 1,2-dichloro-1,2,3,3-tetrafluoropropane, 1-propanethiol, chlorobromomethane, 2-chlorobutane, isopropyl formate, diisopropyl ether, 1,3-dichloro-1,1,3,3-tetrafluoropropane, hexane, 1,3-dichloro-1,2,2,3-tetrafluoropropane, 1,2-dichloro-1,1,2,3-tetrafluoropropane, 3-bromopropene, 2,3-dichloro-1,1,1,3-tetrafluoropropane, 1,1-dichloro-2-fluoroethane, 1-bromopropane, 1,1-difluoro-1,2,2-trichloroethane, methylglyoxal, 1,1,2-trichloro-1,2-difluoroethane, iodoethane, 2-ethoxy-2-methylpropane, 2-bromo-2-methylpropane, 1,2-dichloro-1-fluoroethane, 1,1,1-trichloroethane, 2,2,2-trifluoroethanol, 1-chloro-3-fluoropropane, 1,1,1-trifluoro-2-propanol, 2,3-dichloro-1,1,1-trifluoropropane, perfluoromethylcyclohexane, tetrachloromethane, 1-butylamine, ethyl acetate, 1-chlorobutane, ethanol, butanone, 2,4-dimethylpentane, cyclohexane, n-propyl formate, 2-ethoxybutane, 2-propanol, acetonitrile, pentafluoro-1-propanol, tert-butanol, perfluoroheptane, 1,3-dichloro-1,1,2-trifluoropropane, 1-methoxy-2-methylbutane, 1,1-dichloro-2,2,3-trifluoropropane, cyclohexene, 2,2-dimethoxypropane, 1,3,3-trichloro-1,1,2,2-tetrafluoropropane, 2-chloro-2-methylbutane, 1,2-dichloroethane, 1-ethoxy-2-methylpropane, diisopropylamine, 2-butanethiol, 1,2-dimethoxyethane, 1,1,1-trichloro-2,2,3,3-tetrafluoropropane, 3-methyl-2-butanamine, 1,1,3-trichloro-1,2,2,3-tetrafluoropropane, 1,3-dichloro-1,2,2-trifluoropropane, trichloroethene, diethoxymethane, 1,1-dichloropropane, 2-methyl-1-propanethiol, isopropyl acetate, 1,2-dichloro-2-fluoropropane, 2-iodopropane, dichlorobromomethane, di-n-propyl ether, 3-pentylamine, n-methylbutylamine, 2-bromobutane, 2,2-difluorotetrachloroethane, diethyl sulfide, 1-ethoxybutane, 1,1,2,2-tetrachloro-1,2-difluoroethane, 1-fluorohexane, 1-methoxy-2-propanamine, 1,3-dichloro-1,2,3-trifluoropropane, 2,3-dichloro-1-propene, 2-methylbutanal, 2-methoxyethanamine, 1,2-dichloropropane, propanol, tert-butyl acetate, propionitrile, 3-chloropentane, trichloroacetaldehyde, 2-allyloxyethanol, butanethiol, isoamyl chloride, 1-methoxypentane, ethyl propionate, 2-butanol, 1,2-dimethoxypropane, isopropyl isobutyl ether, 1,1,1-trichloro-2,2,3-trifluoropropane, methylcyclohexane, 1-chloro-4-fluorobutane, 2,4,4-trimethyl-1-pentene, 1-bromo-3-fluoropropane, dioxane, 1-bromobutane, 3-pentanone, 1,1,2-trichloro-2-fluoroethane, 1,1-diethoxyethane, 2-pentanone, 2-methyl-2-butanol, 1-iodopropane, 2-methoxy-1-propanamine, 1,1,3-trichloro-1,2,2-trifluoropropane, 1,1,3-trichloro-2,2,3-trifluoropropane, trimethoxymethane, 2,2-dichlorobutane, cis-1,3-dichloropropene, n-pentylamine, 1,1-dichloro-2,2-difluoroethyl methyl ether, 2,2,4-trimethyl-2-pentene, bromotrichloromethane, n-methylhydroxylamine, perfluorooctane, 1,1,1,2-tetrachloro-2-fluoroethane, 3,3-dimethyl-2-butanone, 1,3-dioxane, piperidine, 1-bromo-2-chloroethane, isobutanol, 2-bromo-2-methylbutane, dipropylamine, 2,2,3,3-tetraflouro-1-propanol, 2-ethoxyethanamine, triethylfluorosilane, 1-methylcyclohexene, sec-butyl acetate, trans-1,3-dichloropropene, 2-fluorotoluene, 2,2-dimethyl-1-propanol, 1,1,2-trichloroethane, 1,1,1-trichloro-3-fluoropropane, n-methyl-1,2-ethanediamine, 2,2-diethoxypropane, 1,3,5-trioxane, 3,3,3-trichloro-1-propene, 1-chloro-3,3-dimethylbutane, pyridine, 2,3-dimethylhexane, 1,1,1,2-tetrachloro-3,3,3-trifluoropropane, n-methylmorpholine, 3-pentanol, 4-methyl-2-pentanone, 1,2-diaminoethane, isobutyl tert-butyl ether, 2-bromopentane, butyronitrile, 1-butanol, trichloroacetyl chloride, 3-mercapto-1,2-propanediol, 2,3-dichlorobutane, sec-butyl tert-butyl ether, 1-methoxy-2-propanol, 1,1,3,3-tetrachloro-1,2,2-trifluoropropane, 1,2-propanediamine, 2,6-dimethyl-5-heptenal, perfluorobutanoic acid, 1,1,1,3-tetrachloro-2,2,3-trifluoropropane, 1-bromo-3-methylbutane, 1,3-dichloro-trans-2-butene, 1,3-dichloropropane, 1-(dimethylamino)-2-propanol, tetrahydrothiophene, tetrachloroethene, 3-methyl-3-pentanol, 1,2-dibromo-1-fluoroethane, 1,1-diethoxypropane, 1,2,2-trichloropropane, 1-chloro-2-methyl-2-propanol, 2-methoxyethanol, 1,2-dichlorobutane, 4,4,4-trifluorobutanol, 2-ethylbutylamine, perfluorononane, octane, diethyl carbonate, n-butyl acetate, 1-pentanethiol, 1,2,2,3-tetrachloro-3,3-difluoropropane, 2-chloro-1,1-dimethoxyethane, 2-hexanone, n-ethylethylenediamine, 3-fluoropropanol, 5-hexen-2-one, 2,3-dichloro-2-methylbutane, 1,1-diethoxy-n,n-dimethylmethanamine, 2-methylpyridine, 1-bromopentane, 2-methoxy-1-propanol, 1,2-dichloro-2-butene, 1-iodobutane, hexanal, 1-ethoxy-2-propanol, 1,2-dibromoethane, 4-methyl-2-pentanol, chlorobenzene, ethylcyclohexane, bromoacetic acid methyl ester, perfluorooctyl bromide, 1,1,2-trichloropropane, 1,2-octanediol, 4-methyl-2-hexanamine, hexylamine, 2-chloro-1-propanol, methoxycyclohexane, 2-(dimethylamino)ethanol, 1,3-dichlorobutane, cyclohexylamine, n-ethyl-2-dimethylaminoethylamine, ethoxyethanol, pentachlorofluoroethane, 3-hexanol, 2-hexanol, 2-methylpyrazine, 2-ethoxy-1-propanol, 1-pentanol, n-ethylmorpholine, 1-methylpiperazine, 1,4-dimethylbenzene, 1,3-dimethylbenzene, 1,3-propanediamine, di-n-butyl ether, 3,3,4,4,5,5,6,6-octafluoro-1-pentanol, valeronitrile, (methyleneamino)acetonitrile, 1,2-dibromopropane, 1,2,3-trichloropropene, 2-heptanamine, 1,2,3-trimethylcyclohexane, 2,3-dimethylbutanol, 1-ethoxyhexane, 1-chloro-3-bromopropane, perfluoro-n-decane, n,n-diethylethylenediamine, 3-furfural, 2,6-dimethylpyridine, 1,1,3,3-tetrachloro-1-fluoropropane, 1,2-dimethylbenzene, 4-methyl-2-hexanone, 1,1,2,2,3-pentchloro-3,3-difluoropropane, 1,1,1-triethoxyethane, styrene, 1-methoxy-2-acetoxypropane, 4-methylpyridine, n,n'-diethyl-1,2-ethanediamine, 1,1,2,2-tetrachloroethane, 2,6-dimethylmorpholine, 2-ethyl-1-butanol, 1,2-dichloropentane, 2-methyl-1-pentanol, methyl hexanoate, 2-propoxyethanol, 2-aminophenol, 1-propoxy-2-propanol, dimethylethanolamine, isopropyl chloroacetate, n-nonane, 2-heptanone, 1-hexanethiol, 1,1,1,3,3-pentachloro-2,2-difluoropropane, 1,2-propanedithiol, heptanal, dimethylformamide, 2,6-dimethylpyrazine, 2-isopropoxyethanol, diethyl disulfide, 2-methylpiperazine, 1-methylcyclohexanol, 1-bromohexane, cyclohexanone, n,n-di-2-propenyl-2-propen-1-amine, hexachloroethane, 1-heptanamine, 2,3-dimethylpyrazine, 2-ethoxyethyl acetate, 1,2,3-trichloropropane, 3-hydroxybutanal, 1-hexanol, 2-(methylamino)ethanol, 1,4-butanediamine, 2,4-dimethylpyridine, 1-chloro-2-methylbenzene, 2-pyrimidinamine, 2-heptanol, 2-methoxy-3-methylpyrazine, dibutylamine, pentachloroethane, 4-methoxy-4-methylpentan-2-one, 1,4-dichloro-trans-2-butene, 3-ethoxy-1-propanol, 1,1,1,3,3-pentachloro-3-fluoropropane, cyclohexanol, 1,4-dichlorobutane, 3-methoxy-1-butanol, furfural, 3-chlorotoluene, diglyme, 1-chloro-4-methylbenzene, 1,1,1-trichloro-2-propanol, 2-(diethylamino)ethanol, 3-methoxypropanenitrile, 2,2-diethoxyethanamine, 1,3,5-trimethylbenzene, 2-methoxy-n-(2-methoxyethyl)ethanamine, n,n,n',n'-tetraethylmethanediamine, 2-chloropyridine, bromocyclohexane, 2,3-heptanedione, 2-(ethylamino)ethanol, 3-methylcyclohexanol, 1,3-dibromopropane, 2-methylcyclohexanol, 3-octanone, diacetone alcohol, diethylaminopropylamine, 2-ethylhexylamine, 1,3-propanedithiol, thiophenol, 1,2,4-trimethylbenzene, ethoxybenzene, 1-butoxy-2-propanol, 2-furanmethanol, 2-butoxyethanol, ethanolamine, methyl acetoacetate, 2-octanone, 2-aminopropanol, 1,4-dichlorobenzene, methyl heptanoate, triethylenediamine, n-decane, n,n-dimethylpropanamide, 2-chlorophenol, 2-amino-1-butanol, 1,3-dichloro-2-propanol, 1-heptanol, 2-methyl-2-nitro-1-propanol, 2-propyl-1-methoxypropanoate, perfluoro-n-dodecane, 1,5-pentanediamine, 1-methyl-2-isopropylbenzene, 2-octanol, cycloheptanone, 1,1,1,2,3-pentachloropropane, 3,4-dimethylpyridine, 1-octanamine, 1,2-dichlorobenzene, 1,1,1,2,2,3-hexachloro-3-fluoropropane, benzylmethylamine, n,n-dimethylbenzylamine, dimethyl malonate, phenol, diiodomethane, 1-chlorooctane, cyclohexanemethanol, 1,1,3,3-tetramethoxypropane, 1-chloro-2,4-dimethylbenzene, 2-(ethylthio)ethanol, 1-ethoxy-2-methylbenzene, aniline, 1-bromo-4-methylbenzene, 2-ethyl-1-hexanol, tert-butylcyclohexylamine, dihexyl phthalate, 1-fluorodecane, 2-chloro-1,4-dimethylbenzene, propylene glycol, dimethyl sulfate, dimethyl sulfoxide, diethylpropanolamine, 2-methylphenol, 2-butoxyethyl acetate, diethyl sulfoxide, 1-octanol, 2-bromopyridine, 2-(2-methoxyethoxy)ethanol, 1,2-butanediol, 2-bromophenol, 4-methylbenzenemethanamine, m-toluenethiol, 1,1,1,2,2,3,3-heptachloro-3-fluoropropane, 1-bromo-4-chlorobenzene, diethylene glycol monoethyl ether, 1,2,4,5-tetramethylbenzene, 2-propylcyclohexanone, 1,4-dibromobutane, trimethyl phosphate, 2-methyl-2,4-pentanediol, 1,3-diethenylbenzene, methyl benzoate, 1-octanethiol, diethyl malonate and 2-methoxypyrimidine.

Advantageously, said organic extracting agent may have a separation factor $S_{1,2}$ of greater than or equal to 1.2 and an adsorption capacity $C_{2,S}$ of greater than or equal to 0.4; and may be chosen from the group consisting of isopropylmethylamine, ethanedial, 2-chloro-2-methylpropane, 2-propanethiol, 2-ethoxypropane, 1-chloro-2,2-difluoropropane, methyl t-butyl ether, diethylamine, propanone, methyl acetate, 1,1-dichloroethane, 4-methoxy-2-methyl-2-butanethiol, 2-bromopropane, chloromethoxymethane, difluorodiethylsilane, 2-butanamine, n-methylpropylamine, tert-butylthiol, isobutanal, tetrahydrofuran, 1-propanethiol, 2-chlorobutane, isopropyl formate, diisopropyl ether, 1-bromopropane, methylglyoxal, 2-ethoxy-2-methylpropane, 2-bromo-2-methylpropane, 1-chloro-3-fluoropropane, 1,1,1-trifluoro-2-propanol, 1-butylamine, ethyl acetate, 1-chlorobutane, ethanol, butanone, n-propyl formate, 2-ethoxybutane, 2-propanol, acetonitrile, tert-butanol, 1-methoxy-2-methylbutane, cyclohexene, 2,2-dimethoxypropane, 2-chloro-2-methylbutane, 1,2-dichloroethane, 1-ethoxy-2-methylpropane, diisopropylamine, 2-butanethiol, 1,2-dimethoxyethane, 3-methyl-2-butanamine, diethoxymethane, 1,1-dichloropropane, 2-methyl-1-propanethiol, isopropyl acetate, 1,2-dichloro-2-fluoropropane, di-n-propyl ether, 3-pentylamine, n-methylbutylamine, 2-bromobutane, diethyl sulfide, 1-ethoxybutane, 1-fluorohexane, 1-methoxy-2-propanamine, 2,3-dichloro-1-propene, 2-methylbutanal, 2-methoxyethanamine, 1,2-dichloropropane, propanol, tert-butyl acetate, propionitrile, 3-chloropentane, trichloroacetaldehyde, 2-allyloxyethanol, butanethiol, isoamyl chloride, 1-methoxypentane, ethyl propionate, 2-butanol, 1,2-dimethoxypropane, isopropyl isobutyl ether, 1-chloro-4-fluorobutane, 2,4,4-trimethyl-1-pentene, 1-bromo-3-fluoropropane, dioxane, 1-bromobutane, 3-pentanone, 1,1-diethoxyethane, 2-pentanone, 2-methyl-2-butanol, 2-methoxy-1-propanamine, trimethoxymethane, 2,2-dichlorobutane, cis-1,3-dichloropropene, n-pentylamine, 3,3-dimethyl-2-butanone, 1,3-dioxane, piperidine, isobutanol, 2-bromo-2-methylbutane, dipropylamine, 2-ethoxyethanamine, triethylfluorosilane, 1-methylcyclohexene, sec-butyl acetate, trans-1,3-dichloropropene, 2,2-dimethyl-1-propanol, 1,1,1-trichloro-3-fluoropropane, n-methyl-1,2-ethanediamine, 2,2-diethoxypropane, 1,3,5-trioxane, 1-chloro-3,3-dimethylbutane, pyridine, n-methylmorpholine, 3-pentanol, 4-methyl-2-pentanone, 1,2-diaminoethane, isobutyl tert-butyl ether, 2-bromopentane, butyronitrile, 1-butanol, 2,3-dichlorobutane, sec-butyl tert-butyl ether, 1-methoxy-2-propanol, 1,2-propanediamine, 2,6-dimethyl-5-heptenal, 1-bromo-3-methylbutane, 1,3-dichloro-trans-2-butene, 1,3-dichloropropane, 1-(dimethylamino)-2-propanol, tetrahydrothiophene, 3-methyl-3-pentanol, 1,1-diethoxypropane, 1,2,2-trichloropropane, 1-chloro-2-methyl-2-propanol, 2-methoxyethanol, 1,2-dichlorobutane, 4,4,4-trifluorobutanol, 2-ethylbutylamine, diethyl carbonate, n-butyl acetate, 1-pentanethiol, 2-chloro-1,1-dimethoxyethane, 2-hexanone, n-ethylethylenediamine, 3-fluoropropanol, 5-hexen-2-one, 2,3-dichloro-2-methylbutane, 1,1-diethoxy-n,n-dimethylmethanamine, 2-methylpyridine, 1-bromopentane, 2-methoxy-1-propanol, 1,2-dichloro-2-butene, hexanal, 1-ethoxy-2-propanol, 4-methyl-2-pentanol, bromoacetic acid methyl ester, 1,2-octanediol, 4-methyl-2-hexanamine, hexylamine, methoxycyclohexane, 2-(dimethylamino)ethanol, 1,3-dichlorobutane, cyclohexylamine, n-ethyl-2-dimethylaminoethylamine, ethoxyethanol, 3-hexanol, 2-hexanol, 2-methylpyrazine, 2-ethoxy-1-propanol, 1-pentanol, n-ethylmorpholine, 1-methylpiperazine, 1,4-dimethylbenzene, 1,3-propanediamine, di-n-butyl ether, valeronitrile, (methyleneamino)acetonitrile, 2-heptanamine, 2,3-dimethylbutanol, 1-ethoxyhexane, 1-chloro-3-bromopropane, n,n-diethylethylenediamine, 3-furfural, 2,6-dimethylpyridine, 4-methyl-2-hexanone, 1,1,1-triethoxyethane, styrene, 1-methoxy-2-acetoxypropane, 4-methylpyridine, n,n'-diethyl-1,2-ethanediamine, 2,6-dimethylmorpholine, 2-ethyl-1-butanol, 1,2-dichloropentane, 2-methyl-1-pentanol, methyl hexanoate, 2-propoxyethanol, 1-propoxy-2-propanol, dimethylethanolamine, isopropyl chloroacetate, 2-heptanone, 1-hexanethiol, 1,2-propanedithiol, heptanal, dimethylformamide, 2,6-dimethylpyrazine, 2-isopropoxyethanol, diethyl disulfide, 2-methylpiperazine, 1-methylcyclohexanol, 1-bromohexane, cyclohexanone, 1-heptanamine, 2,3-dimethylpyrazine, 2-ethoxyethyl acetate, 3-hydroxybutanal, 1-hexanol, 2-(methylamino)ethanol, 1,4-butanediamine, 2,4-dimethylpyridine, 2-pyrimidinamine, 2-heptanol, 2-methoxy-3-methylpyrazine, dibutylamine, 4-methoxy-4-methylpentan-2-one, 1,4-dichloro-trans-2-butene, 3-ethoxy-1-propanol, cyclohexanol, 1,4-dichlorobutane, 3-methoxy-1-butanol, furfural, diglyme, 1,1,1-trichloro-2-propanol, 2-(diethylamino)ethanol, 3-methoxypropanenitrile, 2,2-diethoxyethanamine, 1,3,5-trimethylbenzene, 2-methoxy-n-(2-methoxyethyl)ethanamine, 2-chloropyridine, bromocyclohexane, 2,3-heptanedione, 2-(ethylamino)ethanol, 3-methylcyclohexanol, 1,3-dibromopropane, 2-methylcyclohexanol, 3-octanone, diacetone alcohol, diethylaminopropylamine, 2-ethylhexylamine, 1,3-propanedithiol, ethoxybenzene, 1-butoxy-2-propanol, 2-furanmethanol, 2-butoxyethanol, methyl acetoacetate, 2-octanone, 2-aminopropanol, 1,4-dichlorobenzene, methyl heptanoate, triethylenediamine, n,n-dimethylpropanamide, 2-chlorophenol, 2-amino-1-butanol, 1-heptanol, 2-methyl-2-nitro-1-propanol, 2-propyl-1-methoxypropanoate, 1,5-pentanediamine, 2-octanol, cycloheptanone, 3,4-dimethylpyridine, 1-octanamine, benzylmethylamine, dimethyl malonate, 1-chlorooctane, cyclohexanemethanol, 1,1,3,3-tetramethoxypropane, 2-(ethylthio)ethanol, 1-ethoxy-2-methylbenzene, aniline, 2-ethyl-1-hexanol, tert-butylcyclohexylamine, dihexyl phthalate, 1-fluorodecane, 2-chloro-1,4-dimethylbenzene, dimethyl sulfate, dimethyl sulfoxide, diethylpropanolamine, 2-methylphenol, 2-butoxyethyl acetate, diethyl sulfoxide, 1-octanol, 2-bromopyridine, 2-(2-methoxyethoxy)ethanol, 1,2-butanediol, 2-bromophenol, 4-methylbenzenemethanamine, diethylene glycol monoethyl ether, 1,2,4,5-tetramethylbenzene, 2-propylcyclohexanone, 1,4-dibromobutane, trimethyl phosphate, 2-methyl-2,4-pentanediol, 1,3-diethenylbenzene, methyl benzoate, 1-octanethiol, diethyl malonate and 2-methoxypyrimidine.

Preferably, said organic extracting agent may have a separation factor $S_{1,2}$ of greater than or equal to 1.4 and an adsorption capacity $C_{2,S}$ of greater than or equal to 0.6; and may be chosen from the group consisting of isopropylmethylamine, 2-ethoxypropane, methyl t-butyl ether, diethylamine, propanone, methyl acetate, 4-methoxy-2-methyl-2-butanethiol, 2-butanamine, n-methylpropylamine, isobutanal, tetrahydrofuran, Isopropyl formate, diisopropyl ether, methylglyoxal, 2-ethoxy-2-methylpropane, 1-butylamine, ethyl acetate, butanone, n-propyl formate, 2-ethoxybutane, 2-propanol, tert-butanol, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di-n-propyl ether, 3-pentylamine, n-methylbutylamine, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 2-butanol, 1,2-dimethoxypropane, isopropyl isobutyl ether, dioxane, 3-pentanone, 1,1-diethoxyethane, 2-pentanone, 2-methyl-2-butanol, 2-methoxy-1-propanamine, trimethoxymethane, n-pentylamine, 3,3-dimethyl-2-butanone, 1,3-dioxane, piperidine, isobutanol, dipropylamine, 2-ethoxyethanamine, sec-butyl acetate, 2,2-dimethyl-1-propanol, n-methyl-1,2-ethanediamine, 2,2-diethoxypropane, 1,3,5-trioxane, pyridine, n-methylmorpholine, 3-pentanol, 4-methyl-2-pentanone, 1,2-diaminoethane, butyronitrile, 1-butanol, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-methoxyethanol, 2-ethylbutylamine, diethyl carbonate, n-butyl acetate, 2-chloro-1,1-dimethoxyethane, 2-hexanone, n-ethylethylenediamine, 5-hexen-2-one, 2-methylpyridine, 2-methoxy-1-propanol, hexanal, 1-ethoxy-2-propanol, 4-methyl-2-pentanol, 1,2-octanediol, 4-methyl-2-hexanamine, hexylamine, methoxycyclohexane, 2-(dimethylamino)ethanol, cyclohexylamine, n-ethyl-2-dimethylaminoethylamine, ethoxyethanol, 3-hexanol, 2-hexanol, 2-methylpyrazine, 2-ethoxy-1-propanol, 1-pentanol, n-ethylmorpholine, 1-methylpiperazine, 1,3-propanediamine, di-n-butyl ether, valeronitrile, (methyleneamino)acetonitrile, 2-heptanamine, 2,3-dimethylbutanol, 1-ethoxyhexane, n,n-diethylethylenediamine, 3-furfural, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, 2-ethyl-1-butanol, 2-methyl-1-pentanol, methyl hexanoate, 2-propoxyethanol, 1-propoxy-2-propanol, dimethylethanolamine, isopropyl chloroacetate, 2-heptanone, heptanal, dimethylformamide, 2,6-dimethylpyrazine, 2-isopropoxyethanol, 2-methylpiperazine, 1-methylcyclohexanol, cyclohexanone, 1-heptanamine, 2,3-dimethylpyrazine, 2-ethoxyethyl acetate, 1-hexanol, 2-(methylamino)ethanol, 1,4-butanediamine, 2,4-dimethylpyridine, 2-heptanol, 2-methoxy-3-methylpyrazine, dibutylamine, 4-methoxy-4-methylpentan-2-one, 3-ethoxy-1-propanol, cyclohexanol, 3-methoxy-1-butanol, furfural, diglyme, 2-(diethylamino)ethanol, 3-methoxypropanenitrile, 2,2-diethoxyethanamine, 2-methoxy-n-(2-methoxyethyl)ethanamine, 2,3-heptanedione, 2-(ethylamino)ethanol, 3-methylcyclohexanol, 2-methylcyclohexanol, 3-octanone, diacetone alcohol, diethylaminopropylamine, 2-ethylhexylamine, 1-butoxy-2-propanol, 2-butoxyethanol, methyl acetoacetate, 2-octanone, 2-aminopropanol, methyl heptanoate, triethylenediamine, n,n-dimethylpropanamide, 2-amino-1-butanol, 1-heptanol, 2-propyl-1-methoxypropanoate, 1,5-pentanediamine, 2-octanol, cycloheptanone, 3,4-dimethylpyridine, 1-octanamine, benzylmethylamine, dimethyl malonate, cyclohexanemethanol, 1,1,3,3-tetramethoxypropane, 2-(ethylthio)ethanol, 2-ethyl-1-hexanol, tert-butylcyclohexylamine, dihexyl phthalate, diethylpropanolamine, 2-butoxyethyl acetate, diethyl sulfoxide, 1-octanol, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine.

In particular, said organic extracting agent may have a separation factor $S_{1,2}$ of greater than or equal to 1.6 and an adsorption capacity $C_{2,S}$ of greater than or equal to 0.8; and may be chosen from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, tert-butanol, 2,2-dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, 2-allyloxyethanol, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 3-pentanol, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 1,2-octanediol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, dimethylethanolamine, 2-heptanone, dimethylformamide, 2-isopropoxyethanol, 2-methylpiperazine, cyclohexanone, 1-heptanamine, 2-ethoxyethyl acetate, 2-(methylamino)ethanol, 1,4-butanediamine, 2,4-dimethylpyridine, 2-heptanol, 2-methoxy-3-methylpyrazine, 4-methoxy-4-methylpentan-2-one, 3-ethoxy-1-propanol, cyclohexanol, 3-methoxy-1-butanol, diglyme, 2-(diethylamino)ethanol, 2,2-diethoxyethanamine, 2-methoxy-n-(2-methoxyethyl)ethanamine, 2-(ethylamino) ethanol, 2-methylcyclohexanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-amino-1-butanol, 2-propyl-1-methoxypropanoate, 1,5-pentanediamine, cycloheptanone, 3,4-dimethylpyridine, 1-octanamine, benzylmethylamine, dimethyl malonate, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine.

More particularly, said organic extracting agent may have a separation factor $S_{1,2}$ of greater than or equal to 1.6 and an adsorption capacity $C_{2,S}$ of greater than or equal to 1.0 and may be chosen from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-n-(2-methoxyethyl)ethanamine, 2-(ethylamino) ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-propyl-1-methoxypropanoate, 1,5-pentanediamine, cycloheptanone, 3,4-dimethylpyridine, 1-octanamine, benzylmethylamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine.

Preferentially, said organic extracting agent may be chosen from the group consisting of diethylamine, propanone, methyl acetate, tetrahydrofuran, ethyl acetate, butanone, diethoxymethane, isopropyl acetate, tert-butyl acetate, dioxane, 3-pentanone, 1,1-diethoxyethane, 2-pentanone, n-pentylamine, 1,3-dioxane, sec-butyl acetate, 1,2-diaminoethane, 1-methoxy-2-propanol, n-butyl acetate and 1-ethoxy-2-propanol.

Said first composition may be an azeotropic or quasi-azeotropic composition comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa).

Said first composition may be an azeotropic or quasi-azeotropic composition comprising 2-chloro-3,3,3-trifluoropropene (1233xf) and at least two or all of the compounds chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). The content of each of the compounds in the first azeotropic or quasi-azeotropic composition is as expressed above.

In particular, said first composition may be an azeotropic or quasi-azeotropic composition comprising 2-chloro-3,3,3-trifluoropropene (1233xf) and 1,1,1,3,3-pentafluoropropane (245fa). The content of each of the compounds in this particular composition is as expressed above with reference to the individual contents of each of the compounds. Said azeotropic or quasi-azeotropic composition is obtained at a given temperature and a given pressure. Preferably, said azeotropic or quasi-azeotropic composition may comprise from 45 mol % to 65 mol % of 2-chloro-3,3,3-trifluoropropene (1233xf) and from 35 mol % to 55 mol % of 1,1,1,3,3-pentafluoropropane (245fa) relative to the total composition. Thus, the second composition may comprise 2-chloro-3,3,3-trifluoropropene (1233xf) and 1,1,1,3,3-pentafluoropropane (245fa) and said organic extracting agent as defined above when the separation factor and the absorption capacity are calculated with 1,1,1,3,3-pentafluoropropane (245fa) as second compound of the binary couple.

According to a particular embodiment, said first composition may be an azeotropic or quasi-azeotropic composition comprising 2-chloro-3,3,3-trifluoropropene (1233xf) and E-1-chloro-3,3,3-trifluoro-1-propene (1233zdE). The content of each of the compounds in this particular composition is as expressed above with reference to the individual contents of each of the compounds. Thus, the second composition may comprise 2-chloro-3,3,3-trifluoropropene (1233xf), E-1-chloro-3,3,3-trifluoropropene (1233zdE) and said organic extracting agent, preferably having a separation factor $S_{1,2}$ of greater than or equal to 1.1, advantageously greater than or equal to 1.2, preferably greater than or equal to 1.4, more preferentially greater than or equal to 1.6, in particular greater than or equal to 1.8 and more particularly greater than or equal to 2.0; and/or said organic extracting agent may have an absorption capacity $C_{2,S}$ of greater than or equal to 0.20, advantageously greater than or equal to 0.40, preferably greater than or equal to 0.60, more preferentially greater than or equal to 0.80, in particular a greater than or equal to 1.0, more particularly greater than or equal to 1.4 and preferentially greater than or equal to 1.6. Said organic extracting agent may be as defined above when the separation factor and the absorption capacity are calculated with E-1-chloro-3,3,3-trifluoropropene (1233zdE) as second compound of the binary couple.

According to a preferred embodiment, said third composition comprising the organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) may be subjected to distillation to separate the organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). Said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) may be sent to an incinerator or a device for purifying one of the compounds.

According to a particular embodiment, the stream comprising 2-chloro-3,3,3-trifluoropropene separated out in step b) of the present process is recycled to be used in a process for producing 2,3,3,3-tetrafluoropropene. This makes it possible to improve the overall efficiency of the process since 2-chloro-3,3,3-trifluoropropene can form 2,3,3,3-tetrafluoropropene by fluorination. Preferably, in this embodiment, traces of organic extracting agent may be present in the stream comprising 2-chloro-3,3,3-trifluoropropene. Preferably, the organic extracting agent is chosen so as to prevent or minimize deactivation of the catalyst used in the process for producing 2,3,3,3-tetrafluoropropene.

The present process thus makes it possible to purify 2-chloro-3,3,3-trifluoropropene. Advantageously, the content of at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) in the stream comprising 2-chloro-3,3,3-trifluoropropene, obtained from step b) of the present purification process, is less than the content of that or those in said first composition. For example, the content of any one of the compounds may be reduced by 50%, advantageously by 75%, preferably by 90%, in particular by 95% and more particularly by 98%. The contents are expressed as weight percentages. Preferably, the stream comprising 2-chloro-3,3,3-trifluoropropene obtained in step b) of the present of purification process may be free of said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) when this or these compounds are present in said first composition. The term "free of" means that the stream comprising 2-chloro-3,3,3-trifluoropropene comprises less than 50 ppm, advantageously less than 20 ppm and preferably less than 10 ppm of the compound under consideration on the basis of the total weight of the stream.

According to a preferred embodiment, said first composition used in step a) of the present process is obtained in the course of the implementation of a process for producing 2,3,3,3-tetrafluoropropene, from a purge of the loop. The purge of the reaction loop or a part thereof may be purified beforehand before being used in the present process for purifying 2-chloro-3,3,3-trifluoropropene, for example if the latter is derived from a fluorination or dehydrofluorination reaction. In this case, the purge of the reaction loop or a part thereof would comprise HF, 1,1,1,2,2-pentafluoropropane (245cb), 1,3,3,3-tetrafluoro-1-propene (1234ze), 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). Thus, the present process may comprise, before step a), the following steps:

i') low-temperature separation of said liquid composition to form a first HF-rich phase and a second organic phase containing 1,1,1,2,2-pentafluoropropane (245cb), 1,3,3,3-tetrafluoro-1-propene (1234ze), 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);

ii') distillation of said second organic phase to form and recover, advantageously at the top of the distillation column, a first stream containing 1,1,1,2,2-pentafluoropropane (245cb) and 1,3,3,3-tetrafluoro-1-propene (1234ze), and to form and recover, advantageously at the bottom of the distillation column, a second stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);

iii') recovery of said second stream corresponding to said first composition used in step a) of the present process for purifying 2-chloro-3,3,3-trifluoropropene (1233xf).

The first stream containing 1,1,1,2,2-pentafluoropropane (245cb) and 1,3,3,3-tetrafluoro-1-propene (1234ze) formed and recovered in step ii') may be recycled into the reaction loop, i.e. recycled into step A) below.

Optionally, if the second stream recovered in step ii') contains heavy impurities, they may be removed by distillation. In this case, the heavy impurities are recovered at the bottom of the distillation column, and the second stream corresponding to said first composition used in step a) of the present process for purifying 2-chloro-3,3,3-trifluoropropene (1233xf) is recovered at the top of the distillation column. The heavy impurities may be subsequently incinerated.

According to a second aspect, the present invention provides a process for producing 2,3,3,3-tetrafluoro-1-propene. In addition, this process may include the purification of 2-chloro-3,3,3-trifluoropropene in order to recycle it in a fluorination reaction for the production of 2,3,3,3-tetrafluoro-1-propene. Thus, the present invention provides a process for producing 2,3,3,3-tetrafluoro-1-propene, comprising the steps of:

A) in a reactor, fluorination in the presence of a catalyst for a compound of formula $CX(Y)_2—CX(Y)_m—CH_mXY$ (I) in which X and Y independently represent H, F or Cl and m=0 or 1; and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 1,1,1,2,2-pentafluoropropane, 2-chloro-3,3,3-trifluoropropene, and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), C) distillation of the stream recovered in step B) and recovery, at the top of the distillation column, of a stream comprising 1,1,1,2,2-pentafluoropropane and, at the bottom of the distillation column, of a stream comprising 2-chloro-3,3,3-trifluoropropene (1233xf)

and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), D) performing the process for purifying 2-chloro-3,3,3-trifluoropropene according to the present invention using the stream recovered in step C) and comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa); and E) recycling into step A) the stream comprising the 2-chloro-3,3,3-trifluoropropene formed and recovered in step b) of the purification process performed in step D).

The stream comprising 1,1,1,2,2-pentafluoropropane recovered in step C) may be recycled into step A).

Thus, the process for producing 2,3,3,3-tetrafluoro-1-propene, comprising the steps of:
- A) in a reactor, fluorination in the presence of a catalyst for a compound of formula $CX(Y)_2$—$CX(Y)_m$—$CH_mXY$ (I) in which X and Y independently represent H, F or Cl and m=0 or 1; and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
- B) recovery of a stream comprising 1,1,1,2,2-pentafluoropropane, 2-chloro-3,3,3-trifluoropropene, and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
- C) distillation of the stream recovered in step B) and recovery, at the top of the distillation column, of a stream comprising 1,1,1,2,2-pentafluoropropane and, at the bottom of the distillation column, of a stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
- D) performing the process for purifying 2-chloro-3,3,3-trifluoropropene according to the present invention using the stream recovered in step C) and comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa); comprising the steps of:
  - a) placing the stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) in contact with at least one organic extracting agent to form a second composition;
  - b) extractive distillation of said second composition to form:
    - i) a third composition comprising said organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa),
    - ii) a stream comprising 2-chloro-3,3,3-trifluoropropene;
  - c) recovering and separating out said third composition comprising a stream comprising said organic extracting agent and a stream comprising said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
- E) recycling into step A) the stream comprising the 2-chloro-3,3,3-trifluoropropene formed and recovered in step b) of the purification process performed in step D).

Preferably, the organic extracting agent separated out in step c) may be recycled into step a).

Preferably, the stream comprising said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) separated out in step c) may be recovered to be incinerated or to purify one or more constituents thereof, for example E-1-chloro-3,3,3-trifluoro-1-propene (1233zdE) or 1,1,1,3,3-pentafluoropropane (245fa).

According to a preferred embodiment, the stream recovered in step B) also comprises HF and 1,3,3,3-tetrafluoro-1-propene (1234ze), the latter being, prior to performing the distillation of step C), treated according to the following steps:
- i') low-temperature separation of said stream to form a first HF-rich phase and a second organic phase containing 1,1,1,2,2-pentafluoropropane (245cb), 1,3,3,3-tetrafluoro-1-propene (1234ze), 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
- ii') distillation of said second organic phase to form and recover, advantageously at the top of the distillation column, a first stream containing 1,1,1,2,2-pentafluoropropane (245cb) and 1,3,3,3-tetrafluoro-1-propene (1234ze), and to form and recover, advantageously at the bottom of the distillation column, a second stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
- iii') recovery of said second stream and implementation of step D) using same.

The first stream containing 1,1,1,2,2-pentafluoropropane (245cb) and 1,3,3,3-tetrafluoro-1-propene (1234ze) formed and recovered in step ii') may be recycled into step A).

More particularly, step A) is performed starting with 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane, preferably starting with 1,1,1,2,3-pentachloropropane, 1,1,2,3,tetrachloropropene, 1,1,1,2,2-pentafluoropropane and/or 2-chloro-3,3,3-trifluoro-1-propene; in particular starting with 1,1,1,2,3-pentachloropropane (240db).

FIG. 1a schematically represents a device for performing a process for purifying 2-chloro-3,3,3-trifluoropropene (1233xf) according to a particular embodiment of the invention. A composition comprising HF, 1,1,1,2,2-pentafluoropropane (245cb), 1,3,3,3-tetrafluoro-1-propene (1234ze), 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) is provided at 1. The composition may also comprise one or more heavy impurities. The composition is cooled at 2 to form an upper phase comprising HF and a lower organic phase comprising 1,1,1,2,2-pentafluoropropane (245cb), 1,3,3,3-tetrafluoro-1-propene (1234ze), 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa); and heavy impurities. The upper phase comprising HF is recycled to 3, i.e. to the catalytic fluorination reactor, whereas the lower organic phase is transferred via pipe 4 to a distillation column 5. The distillation performed at 5 allows recovery at the top of the distillation column via pipe 7 of a stream comprising 1,1,1,2,2-pentafluoropropane (245cb) and 1,3,3,3-tetrafluoro-1-propene (1234ze), which may be recycled to 3, i.e. to the catalytic fluorination reactor. The stream recovered at the bottom of the distillation column 5 comprises 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa); and heavy impurities. This stream is conveyed via pipe 8 to the distillation column 6 to remove the heavy impurities. These impurities are recovered at the bottom of the distillation column 6 and conveyed to a device 11 via pipe 10. The device 11 may be an incinerator, a thermal oxidizer or a purification device. A stream comprising 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) is recovered at the top of the distillation column 6 and conveyed via pipe 9 to an extractive distillation column 12. This distillation column 12 makes it possible to purify 2-chloro-3,3,3-trifluoropropene (1233xf), which is recovered at the top of the distillation column and recycled via pipe 13 to 3, i.e. to the catalytic fluorination reactor. The extractive distillation column 12 is fed with organic extracting agent 19 via pipe 17. Said organic extracting agent and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) are recovered at the bottom of the extractive distillation column 12 and transferred to a distillation column 15 via pipe 14 to be separated. The organic extracting agent is recovered at the bottom of the distillation column 15 and recycled into the extractive distillation column 12 via pipe 17. Said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) is transferred to a device 11 via pipe 16.

Figure 1B:
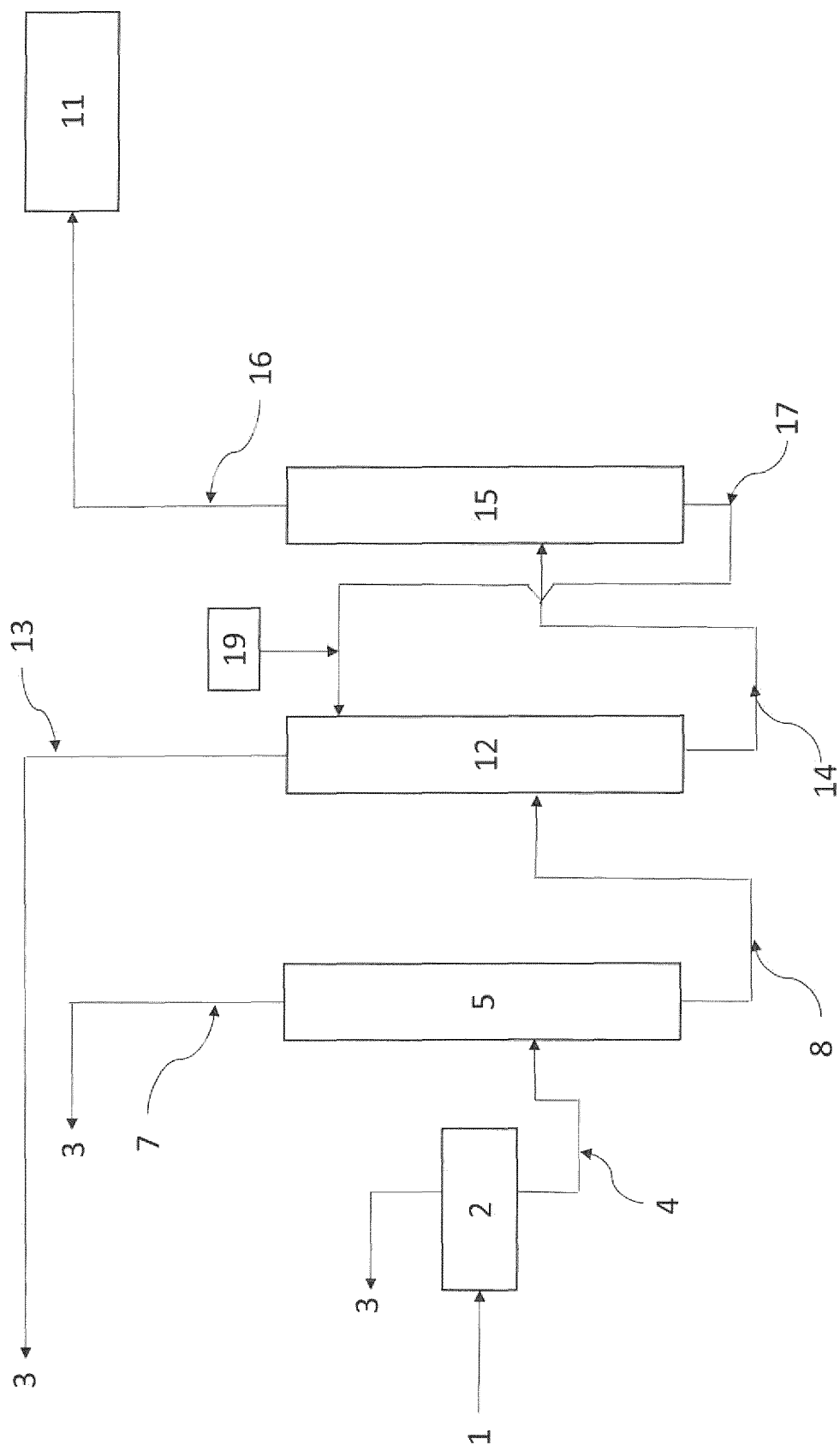

FIG. 1*b* schematically represents a device for performing a process for purifying 2-chloro-3,3,3-trifluoropropene (1233xf) from a composition which does not comprise any heavy impurities. In this particular case, the stream recovered at the bottom of the distillation column 5 comprises 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa). This stream is then conveyed directly to the extractive distillation column 12 via pipe 8.

Figure 1C:
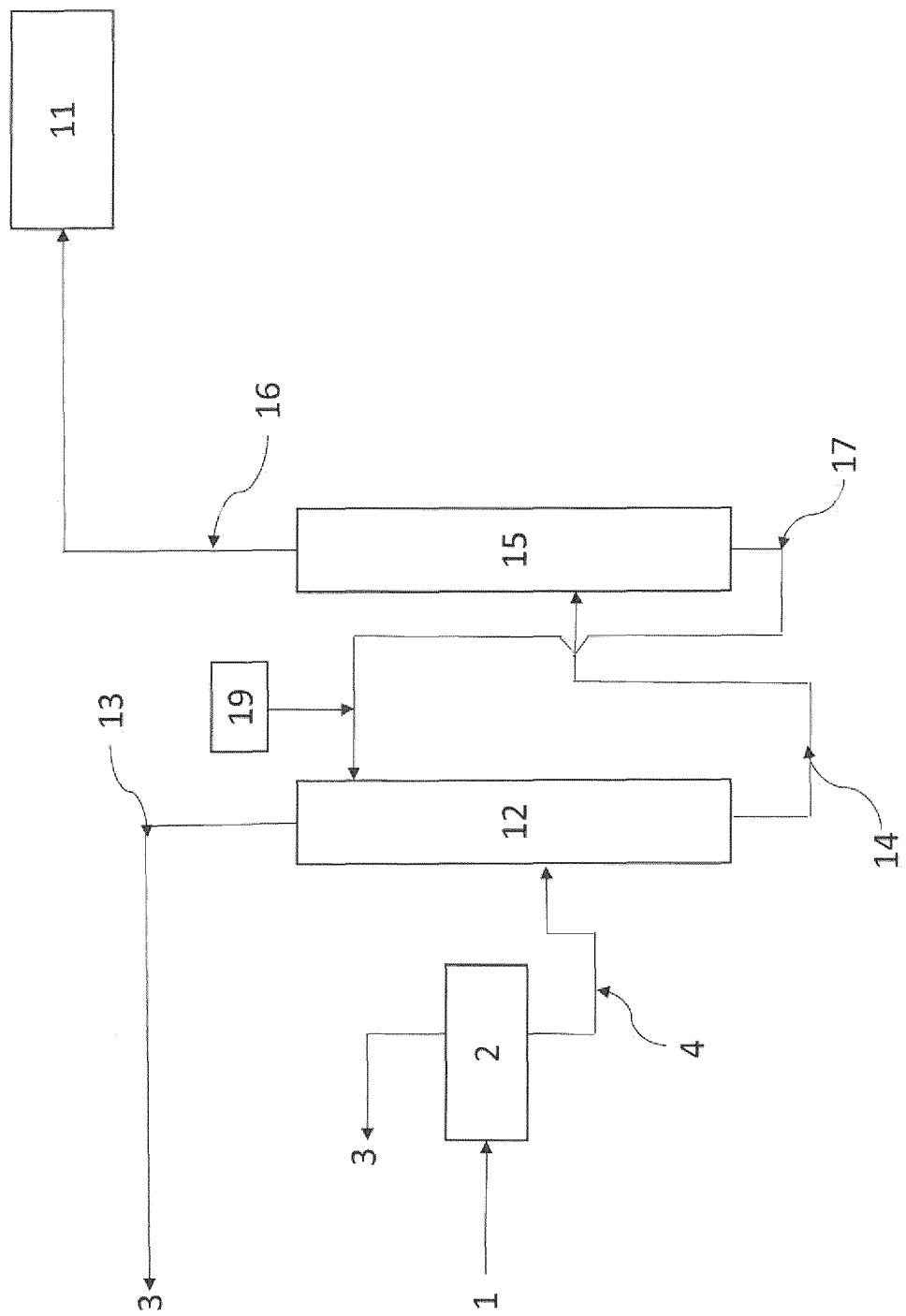

If the lower organic phase recovered at 2 comprises 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) but is free of 1,1,1,2,2-pentafluoropropane (245cb) and 1,3,3,3-tetrafluoro-1-propene (1234ze), then the lower organic phase is conveyed to the extractive distillation column 12 via pipe 4 as illustrated in FIG. 1*c*.

Figure 1D:
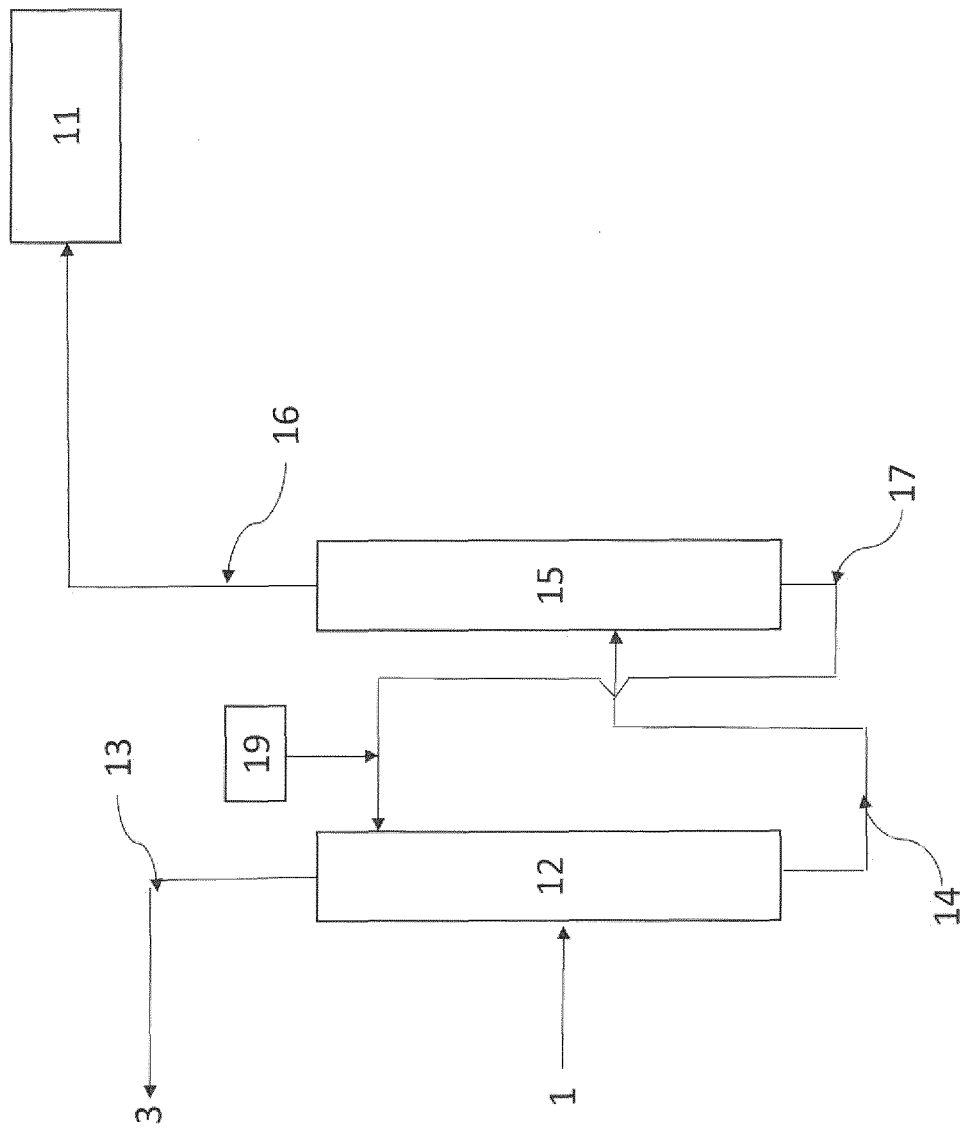

When the composition conveyed to 1 essentially comprises 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa), said composition may be subjected directly to extractive distillation as illustrated in FIG. 1*d* in the presence of organic extracting agent 19. The composition is thus transferred to the extractive distillation column 12 to separate out and recover 2-chloro-3,3,3-trifluoropropene (1233xf) at the top of the distillation column 12, to be recycled to 3 via pipe 13. The organic extracting agent 19 and said at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) are treated as explained in relation with FIG. 1*a*.

Figure 2:
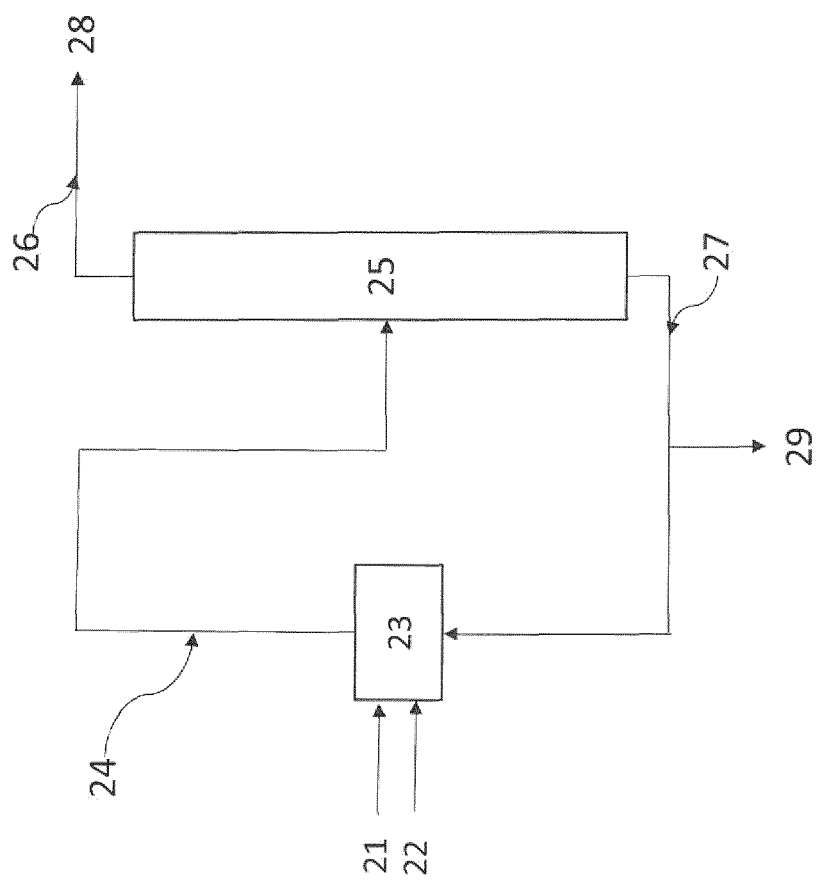
FIG. 2 schematically represents a device for performing a process for producing 2,3,3,3-tetrafluoropropene according to a particular embodiment of the present invention.

FIG. 2 schematically illustrates a device for performing a process for producing 2,3,3,3-tetrafluoropropene according to a particular embodiment of the present invention. Hydrofluoric acid 21 is placed in contact with 1,1,1,2,3-pentachloropropane (240db) 22 in a reactor 23. A stream comprising HF, 2,3,3,3-tetrafluoropropene, HCl, 2-chloro-3,3,3-trifluoropropene (1233xf) and at least one compound chosen from the group consisting of E-1-chloro-3,3,3-trifluoro-1-propene (1233zdE), 1,1,1,3,3-pentafluoropropane (245fa) and 1,1,1,3,3,3-hexafluoropropane (236fa) is recovered at the reactor outlet and conveyed to a distillation column 25. The stream may also comprise heavy impurities, 1,1,1,2,2-pentafluoropropane (245cb) and 1,3,3,3-tetrafluoro-1-propene (1234ze). A stream comprising HCl and 2,3,3,3-tetrafluoropropene is recovered at the top of the distillation column and conveyed via pipe 26 to a purification device 28 that is capable of separating HCl and 2,3,3,3-tetrafluoropropene, for example a distillation column. Part of the stream obtained at the bottom of the distillation column, preferably less than 50% by weight relative to the total weight of the stream obtained at the bottom of the distillation column, is conveyed to the device 29 for purifying 2-chloro-3,3,3-trifluoro-1-propene (1233xf) via pipe 27. The purification device 29 may be any of the devices illustrated in FIGS. 1*a*-1*d*.

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

The catalyst is preferably subjected to activation with air or oxygen and HF at a temperature from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
  with an HF/compound of formula (I) and/or (II) mole ratio from 3:1 to 150:1, preferably from 4:1 to 125:1 and more particularly preferably from 5:1 to 100:1;
  with a contact time from 3 to 100 seconds, preferably 4 to 75 seconds and more particularly 5 to 50 seconds (volume of catalyst divided by the total entering stream, adjusted to the operating temperature and pressure);
  at a pressure ranging from atmospheric pressure to 20 bar, preferably from 2 to 18 bar and more particularly from 3 to 15 bar;
  at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

Method for Selecting the Organic Extracting Agent

The selection of the organic extracting agent is determined by using the Cosmo-RS model implemented in the Cosmotherm software. For this selected binary couple, a separation factor is calculated for each of the solvents studied via the following equation:

$$S_{1,2} = (\gamma_{1,S} * P1)/(\gamma_{2,S} * P2) \text{ in which}$$

$\gamma_{1,S}$ represents the activity coefficient of the first compound 1 in the organic extracting agent under consideration at infinite dilution, P1 represents the saturating vapor pressure of the first compound 1, $\gamma_{2,S}$ represents the activity coefficient of the second compound 2 of the binary couple in the organic extracting agent under consideration at infinite dilution, P2 represents the saturating vapor pressure of the second compound 2.

An absorption capacity is also calculated for each of the solvents studied and for a binary couple (1,2) under consideration. The absorption capacity is calculated via the formula $C_{2,S} = 1/(\gamma_{2,S})$ in which $\gamma_{2,S}$ represents the activity coefficient of the second compound of the binary couple under consideration in said organic extracting agent studied at infinite dilution.

The calculations are repeated for each organic extracting agent studied. Minimum separation factor and absorption capacity values are identified so as to allow a sufficient separation between the first compound and the second compound of the binary couple (1,2) under consideration. The saturating vapor pressure is considered for a temperature of 25° C.

EXAMPLES

Example 1

Separation between 2-chloro-3,3,3-trifluoropropene (1233xf) and 1,1,1,3,3-pentafluoropropane (245fa) is considered. On the basis of the information obtained by the Cosmo-RS model, the solvents given in table 1 below were tested for the extractive distillation of a mixture comprising 2-chloro-3,3,3-trifluoropropene (1233xf) and 1,1,1,3,3-pentafluoropropane (245fa).

TABLE 1 capacity and separation factor of the organic extracting agent

| Organic extracting agent | Absorption capacity | Separation factor |
|---|---|---|
| Propanone | 1.83 | 2.45 |
| Methyl acetate | 2.12 | 2.35 |
| Ethyl acetate | 2.17 | 1.89 |
| Butanone | 1.72 | 1.77 |
| Dioxane | 1.69 | 1.62 |
| Trimethoxymethane | 2.07 | 1.83 |
| 1,3-Dioxane | 1.83 | 1.76 |
| 1,3,5-Trioxane | 1.04 | 2.58 |
| 1,2-Diaminoethane | 1.87 | 2.41 |
| 1-Methoxy-2-propanol | 1.22 | 1.68 |

Example 2

Separation between 2-chloro-3,3,3-trifluoropropene (1233xf) and E-1-chloro-3,3,3-trifluoro-1-propene (1233zdE) is considered. On the basis of the information obtained by the Cosmo-RS model, the solvents given in table 2 below were tested for the extractive distillation of a first composition comprising 2-chloro-3,3,3-trifluoropropene (1233xf) and E-1-chloro-3,3,3-trifluoro-1-propene (1233zdE).

TABLE 2 capacity and separation factor of the organic extracting agent

| Organic extracting agent | Absorption capacity | Separation factor |
|---|---|---|
| Diethylamine | 3.29 | 1.96 |
| Propanone | 1.15 | 1.68 |
| Methyl acetate | 1.42 | 1.70 |
| Tetrahydrofuran | 2.94 | 1.80 |
| Ethyl acetate | 1.86 | 1.76 |
| Butanone | 1.46 | 1.63 |
| Diethoxymethane | 2.30 | 1.63 |
| Isopropyl acetate | 2.04 | 1.71 |
| tert-Butyl acetate | 2.10 | 1.71 |
| Dioxane | 1.78 | 1.85 |
| 3-Pentanone | 1.77 | 1.65 |
| 1,1-Diethoxyethane | 2.49 | 1.67 |
| 2-Pentanone | 1.70 | 1.63 |
| n-Pentylamine | 3.56 | 2.21 |
| 1,3-Dioxane | 1.74 | 1.81 |
| sec-Butyl acetate | 2.14 | 1.69 |
| 1,2-Diaminoethane | 2.74 | 3.81 |
| 1-Methoxy-2-propanol | 2.06 | 1.72 |
| n-Butyl acetate | 2.08 | 1.72 |
| 1-Ethoxy-2-propanol | 1.50 | 1.92 |

Example 3

Separation between, on the one hand, 2-chloro-3,3,3-trifluoropropene (1233xf) and, on the other hand, E-1-chloro-3,3,3-trifluoro-1-propene (1233zdE) and 1,1,1,3,3-pentafluoropropane (245fa) is considered. On the basis of the information obtained by the Cosmo-RS model, the solvents given in table 3 below were tested for the extractive distillation of a first composition comprising 2-chloro-3,3,3-trifluoropropene (1233xf), 1,1,1,3,3-pentafluoropropane (245fa) and E-1-chloro-3,3,3-trifluoro-1-propene (1233zdE).

TABLE 3 capacity and separation factor of the organic extracting agent

| Organic extracting agent organique | Absorption capacity (relative to 245fa) | Separation factor (relative to 245fa) | Absorption capacity (relative to 1233zdE) | Separation factor (relative to 1233zdE) |
|---|---|---|---|---|
| Propanone | 1.83 | 2.45 | 1.15 | 1.68 |
| Methyl acetate | 2.12 | 2.35 | 1.42 | 1.70 |
| Ethyl acetate | 2.17 | 1.89 | 1.86 | 1.76 |
| Butanone | 1.72 | 1.77 | 1.46 | 1.63 |
| Dioxane | 1.69 | 1.62 | 1.78 | 1.85 |
| Trimethoxymethane | 2.07 | 1.83 | 1.76 | 1.68 |
| 1,3-Dioxane | 1.83 | 1.76 | 1.74 | 1.81 |
| 1,2-Diaminoethane | 1.87 | 2.41 | 2.74 | 3.81 |
| 1-Methoxy-2-propanol | 1.21 | 1.69 | 1.26 | 1.90 |
| 3-Methoxy-1-butanol | 1.52 | 1.63 | 1.72 | 1.99 |
| Diacetone alcohol | 1.55 | 1.91 | 1.45 | 1.95 |

The results were confirmed using a mixture comprising 60% to 90% by weight of 2-chloro-3,3,3-trifluoropropene (1233xf), 5% to 25% by weight of 1-chloro-3,3,3-trifluoropropene (1233zd) and 5% to 15% by weight of 1,1,1,3,3-pentafluoropropane (245fa) relative to the total weight of the composition. The rest of the composition is formed by the organic extracting agent tested.

The invention claimed is:

1. A process for purifying 2-chloro-3,3,3-trifluoropropene (1233xf) from a first composition comprising 2-chloro-3,3,3-trifluoropropene and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa), said process comprising:
   a) placing said first composition in contact with at least one organic extracting agent to form a second composition;
   b) distilling said second composition by extractive distillation to form:
      i) a third composition comprising said organic extracting agent and said at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa), and
      ii) a stream comprising 2-chloro-3,3,3-trifluoropropene; and
   c) recovering and separating out said third composition to form a stream comprising said organic extracting agent and a stream comprising said at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa),
   wherein said organic extracting agent has a separation factor $S_{1,2}$ of greater than or equal to 1.1, said separation factor being the formula $S_{1,2}=(\gamma_{1,S}*P1)/(\gamma_{2,S}*P2)$ wherein $\gamma_{1,S}$ represents the activity coefficient of 2-chloro-3,3,3-trifluoropropene in said organic extracting agent at infinite dilution,
   P1 represents the saturating vapor pressure of 2-chloro-3,3,3-trifluoropropene,
   $\gamma_{2,S}$ represents the activity coefficient of said at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa) in said organic extracting agent at infinite dilution, and
   P2 represents the saturating vapor pressure of said at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa), and
   said organic extracting agent has an absorption capacity $C_{2,S}$ of greater than or equal to 0.20,
   said absorption capacity being calculated by the formula $C_{2,S}=1/(\gamma_{2,S})$ in which $\gamma_{2,S}$ represents the activity coefficient of said at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa) in said organic extracting agent at infinite dilution.

2. The process as claimed in claim 1, wherein the stream comprising the organic extracting agent separated out in step c) is recycled into step a).

3. The process as claimed in claim 1, wherein said stream comprising 2-chloro-3,3,3-trifluoropropene formed in step b) is recovered at the top of the distillation column and optionally recycled into a process for producing 2,3,3,3-tetrafluoropropene.

4. The process as claimed in claim 1, wherein said organic extracting agent comprises a solvent selected from the group consisting of hydrocarbon, halohydrocarbon, alcohol, ketone, amine, ester, ether, aldehyde, nitrile, carbonate, sulfoxide, sulfate, thioalkyl, amide, heterocycle and phosphate, or the organic extracting agent comprises perfluorobutanoic acid.

5. The process as claimed in claim 1, wherein said organic extracting agent has a boiling point of between 50 and 200° C.

6. The process as claimed in claim 1, wherein when said at least one compound is 1,1,1,3,3-pentafluoropropane (245fa), said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein $\gamma_{1,S}$ represents the activity coefficient of 2-chloro-3,3,3-trifluoropropene in said organic extracting agent at infinite dilution, P1 represents the saturating vapor pressure of 2-chloro-3,3,3-trifluoropropene, $\gamma_{2,S}$ represents the activity coefficient of 1,1,1,3,3-pentafluoropropane (245fa) in said organic extracting agent at infinite dilution, and P2 represents the saturating vapor pressure of 1,1,1,3,3-pentafluoropropane (245fa); and said organic extracting agent has an absorption capacity $C_{2,S}$ of greater than or equal to 0.20, the absorption capacity being calculated by the formula $C_{2,S}=1/(\gamma_{2,S})$ in which $\gamma_{2,S}$ represents the activity coefficient of 1,1,1,3,3-pentafluoropropane (245fa) in said organic extracting agent at infinite dilution.

7. The process as claimed in claim 6, wherein said organic extracting agent is selected from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, n,n-dimethylpropanamide, dimethyl malonate, diethyl sulfoxide, 2-(2-methoxyethoxy)ethanol, trimethyl phosphate and diethyl malonate.

8. The process as claimed in claim 1, wherein when said at least one compound is E-1-chloro-3,3,3-trifluoro-1-propene (1233zdE), said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein $\gamma_{1,S}$ represents the activity coefficient of 2-chloro-3,3,3-trifluoropropene in said organic extracting agent at infinite dilution, P1 represents the saturating vapor pressure of 2-chloro-3,3,3-trifluoropropene, $\gamma_{2,S}$ represents the activity coefficient of E-1-chloro-3,3,3-trifluoro-1-propene (1233zdE) in said organic extracting agent at infinite dilution, P2 represents the saturating vapor pressure of E-1-chloro-3,3,3-trifluoro-1-propene (1233zdE); and said organic extracting agent has an absorption capacity $C_{2,S}$ of greater than or equal to 0.20, said absorption capacity being calculated by the formula $C_{2,S}=1/(\gamma_{2,S})$ wherein $\gamma_{2,S}$ represents the activity coefficient of E-1-chloro-3,3,3-trifluoro-1-propene (1233zdE) in said organic extracting agent at infinite dilution.

9. The process as claimed in claim 8, wherein said organic extracting agent is selected from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-n-(2-methoxyethyl) ethanamine, 2-(ethylamino)ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-propyl-1-methoxypropanoate, 1,5-pentanediamine, cycloheptanone, 3,4-dimethylpyridine, 1-octanamine, benzylmethylamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine.

10. The process as claimed in claim 1, wherein said organic extracting agent is selected from the group consisting of propanone, methyl acetate, ethyl acetate, butanone, dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, n,n- dimethylpropanamide, diethyl sulfoxide, 2-(2-methoxyethoxy)ethanol, trimethyl phosphate and diethylmalonate.

11. The process as claimed in claim 1, wherein the first composition is an azeotropic or quasi-azeotropic composition comprising 2-chloro-3,3,3-trifluoropropene and E-1-chloro-3,3,3-trifluoro-1-propene (1233zdE); or the first composition is an azeotropic or quasi-azeotropic composition comprising 2-chloro-3,3,3-trifluoropropene and 1,1,1,3,3-pentafluoropropane (245fa).

12. A process for producing 2,3,3,3-tetrafluoro-1-propene, comprising:
   A) in a reactor, fluorination in the presence of a catalyst for a compound of formula (I) $CX(Y)_2$—$CX(Y)_m$—$CH_m XY$ in which X and Y independently represent a hydrogen, fluorine or chlorine atom and m=0 or 1; and/or catalytic fluorination in the presence of a catalyst for a compound of formula $(CX_n Y_{3-n})CH_p X_{1-p} CH_m X_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
   B) recovering a stream derived from purging of a recycling reaction loop, comprising 1,1,1,2,2-pentafluoropropane, 2-chloro-3,3,3-trifluoropropene, and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
   C) distilling the stream recovered in step B) and recovery, at the top of a distillation column, of a stream comprising 1,1,1,2,2-pentafluoropropane and, at the bottom of the distillation column, of a stream comprising 2-chloro-3,3,3-trifluoropropene (1233xf) and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
   D) performing the process for purifying 2-chloro-3,3,3-trifluoropropene as claimed in claim 1 using the stream recovered in step C) and comprising 2-chloro-3,3,3-trifluoropropene (1233xf) and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa); and
   E) recycling into step A) the stream comprising the 2-chloro-3,3,3-trifluoropropene formed and recovered in step b) of the purification process performed in step D).

13. The process as claimed in the claim 12, wherein the stream recovered in step B) also comprises HF, 1,1,1,2,2-pentafluoropropane and 1,3,3,3-tetrafluoro-1-propene (1234ze), the latter being, prior to performing the distillation of step C), treated as follows:
   i) low-temperature separation of a liquid composition to form a first HF-rich phase and a second organic phase comprising 1,1,1,2,2-pentafluoropropane, 1,3,3,3-tetrafluoro-1-propene (1234ze), 2-chloro-3,3,3-trifluoropropene (1233xf) and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
   ii) distilling said second organic phase to form and recover, at the top of the distillation column, a first stream comprising 1,1,1,2,2-pentafluoropropane and 1,3,3,3-tetrafluoro-1-propene (1234ze), and to form and recover, at the bottom of the distillation column, a second stream comprising 2-chloro-3,3,3-trifluoropropene (1233xf) and at least one compound selected from the group consisting of E-1-chloro-3,3,3-trifluoro-1-propene (1233zdE), 1,1,1,3,3-pentafluoropropane (245fa) and 1,1,1,3,3,3-hexafluoropropane (236fa);
   iii) recovering said second stream and implementing step D) using same.

14. A composition comprising 2-chloro-3,3,3-trifluoropropene (1233xf), 1,1,1,3,3-pentafluoropropane (245fa) and an organic extracting agent with a separation factor $S_{1,2}$ of greater than or equal to 1.6, said separation factor being calculated by the formula $S_{1,2}=(\gamma_{1,S}*P1)/(\gamma_{2,S}*P2)$ wherein $\gamma_{1,S}$ represents the activity coefficient of 2-chloro-3,3,3-trifluoropropene (1233xf) in said organic extracting agent at infinite dilution, P1 represents the saturating vapor pressure of 2-chloro-3,3,3-trifluoropropene (1233xf), $\gamma_{2,S}$ represents the activity coefficient of 1,1,1,3,3-pentafluoropropane (245fa) in said organic extracting agent at infinite dilution, and P2 represents the saturating vapor pressure of 1,1,1,3,3-pentafluoropropane (245fa).

15. A composition comprising 2-chloro-3,3,3-trifluoropropene (1233xf), E-1-chloro-3,3,3-trifluoro-1-propene (1233zdE) and an organic extracting agent with a separation factor $S_{1,2}$ of greater than or equal to 1.6, said separation factor being calculated by the formula $S_{1,2}=(\gamma_{1,S}*P1)/(\gamma_{2,S}*P2)$ in which $\gamma_{1,S}$ represents the activity coefficient of 2-chloro-3,3,3-trifluoropropene (1233xf) in said organic extracting agent at infinite dilution, P1 represents the saturating vapor pressure of 2-chloro-3,3,3-trifluoropropene (1233xf), $\gamma_{2,S}$ represents the activity coefficient of E-1-chloro-3,3,3-trifluoro-1-propene (1233zdE) in said organic extracting agent at infinite dilution, and P2 represents the saturating vapor pressure of E-1-chloro-3,3,3-trifluoro-1-propene (1233zdE).

* * * * *